(12) United States Patent
Prokai et al.

(10) Patent No.: US 7,534,779 B2
(45) Date of Patent: May 19, 2009

(54) QUINOL COMPOUND AND PHARMACEUTICAL COMPOSITION

(75) Inventors: Laszlo Prokai, Mansfield, TX (US); Katalin Prokai, Mansfield, TX (US)

(73) Assignees: University of Florida, Gainesville, FL (US); University of North Texas Health Science Center, Fort Worth, TX (US)

( * ) Notice: Subject to any disclaimer, the term of this patent is extended or adjusted under 35 U.S.C. 154(b) by 31 days.

(21) Appl. No.: 11/838,676

(22) Filed: Aug. 14, 2007

(65) Prior Publication Data

US 2008/0119446 A1     May 22, 2008

Related U.S. Application Data

(63) Continuation of application No. 11/682,072, filed on Mar. 5, 2007, now abandoned, which is a continuation-in-part of application No. 10/731,528, filed on Dec. 9, 2003, now Pat. No. 7,186,707, application No. 11/838,676, which is a continuation-in-part of application No. 10/405,413, filed on Apr. 1, 2003, now Pat. No. 7,026,306.

(60) Provisional application No. 60/369,589, filed on Apr. 1, 2002, provisional application No. 60/432,354, filed on Dec. 9, 2002.

(51) Int. Cl.
*A61K 31/56* (2006.01)
*C07J 1/00* (2006.01)

(52) U.S. Cl. .................. 514/178; 562/612; 562/627

(58) Field of Classification Search ............... 552/612, 552/627; 514/178
See application file for complete search history.

(56) References Cited

U.S. PATENT DOCUMENTS

| | | | |
|---|---|---|---|
| 2,910,486 A | 10/1959 | Jiu | |
| 2,950,291 A | 8/1960 | Jiu | |
| 5,041,434 A | 8/1991 | Lubkin | |
| 5,108,996 A | 4/1992 | Claussner et al. | |
| 5,395,831 A | 3/1995 | Gemmill, Jr. et al. | |
| 5,405,944 A | 4/1995 | Suzuki et al. | |
| 5,552,395 A | 9/1996 | Gemmill, Jr. et al. | |
| 5,554,601 A | 9/1996 | Simpkins et al. | |
| 5,646,136 A | 7/1997 | Petrow et al. | |
| 5,859,001 A | 1/1999 | Simpkins et al. | |
| 5,891,878 A | 4/1999 | Beasley et al. | |
| 6,096,733 A | 8/2000 | Lubkin | |
| 6,197,833 B1 | 3/2001 | Simpkins et al. | |
| 6,258,856 B1 | 7/2001 | Chamberlain et al. | |
| 6,319,914 B1 | 11/2001 | Simpkins et al. | |
| 2002/0016340 A1 | 2/2002 | Rosati | |
| 2003/0050295 A1 | 3/2003 | Pang | |
| 2003/0105167 A1* | 6/2003 | Dykens et al. ............ | 514/732 |
| 2004/0214806 A1 | 10/2004 | Pang et al. | |

FOREIGN PATENT DOCUMENTS

| | | |
|---|---|---|
| DE | 196 54 750 A1 | 7/1998 |
| WO | WO 02/36605 | 5/2002 |
| WO | WO 03/084978 | 10/2003 |

OTHER PUBLICATIONS

Beers, M.H. and R. Berkow, Editors, The Merck Manual of diagnosis and therapy, pp. 471-473 and pp. 1942-1944 (1999) Merck Research Laboratories, Whitehouse Station, N.J. USA.

Bigsby, R.M. et al. "Protective Effects of Estrogen in a Rat Model of Age-Related Cataracts" *Proc. Natl. Acad. Sci.*, Aug. 1999, pp. 9328-9332, vol. 96.

Breuer, H. and Koster, G., "Interaction Between Oestrogens and Neurotransmitters at the Hypophysial-Hypothalamic Level", *Journal of Steroid Biochemistry*, 1974, pp. 961-967, vol. 5, Pergamon Press, Great Britain.

Galdecki, Z. et al., "Structure of 2,4-Dibromo-10β, 17β-dihydroxy-1,4-estradien-3-one", *Acta Cryst.*, 1987, pp. 967-968, vol. C43, International Union of Crystallography.

Hiemke, C. et al., "Actions of Sex Hormones on the Brian", *Prog. Neuro-Psychopharmacol & Biol. Psychiat.*, 1992, pp. 377-388, vol. 16, Pergamon Press, Great Britain.

Kupfer, R. et al., "Comparisons of Hydroperoxide Isomerase and Monooxygenase Activities of Cytochrome P450 for Conversions of Allylic Hydroperoxides and Alcohols to Epxyalcohols and Diols: Probing Substrate Reorientation in the Active Site", *Biochemistry*, 2001, pp. 11490-11501, vol. 10, American Chemical Society.

Liang, Y. et al., "Membrane Fluidity Effects of Estratrienes", *Brain Research Bulletin*, 2001, pp. 661-668, vol. 54, No. 6, Elsevier Science Inc., USA.

(Continued)

*Primary Examiner*—Barbara P Badio
(74) *Attorney, Agent, or Firm*—Saliwanchik, Lloyd & Saliwanchik

(57) ABSTRACT

The subject invention provides a mechanism by which steroidal quinol compounds confer beneficial ophthalmic effects. The subject compounds possess a lipophilic-hydrophilic balance for transcorneal penetration and are readily reduced into parent phenolic A-ring steroid compounds to provide protection or treatment against various ocular symptoms and disorders. The compounds according to the subject invention appear to be highly advantageous as prodrugs to provide protection and/or treatment against ocular disorders. These prodrugs confer lipid solubility optimal for transcorneal penetration and are readily converted to endogenous reducing agents into active phenolic A-ring steroid compounds. To the extent that these prodrugs have reduced feminizing effects and systemic toxicity, they would be expected to be quite advantageous for protecting or treating the eye against ocular disorders such as cataract or glaucoma without undesired (systemic) side effects).

2 Claims, 4 Drawing Sheets

OTHER PUBLICATIONS

Lunn et al., "The adamantyl carbonium ion as a dehydrogenating agent, its reactions with estrone," *Tetrahedron*, 1968, vol. 24, No. 23, pp. 6773-6776.

Lupon, P. et al. (1983) "Photooxygenierung von Oestrogenen: Eine Neu 19-Norsteroid-Synthese" Verlagsgesellscaft, Weinheim, DE, vol. 95, No. 9, p. 757.

McCullough, L. and Hurn, P., "Estrogen and Ischemic Neuroprotection: an intergrated view", *Trends in Endocrinology and Metabolism*, Jul. 2003, pp. 238-235, vol. 14, No. 5, Elsevier Science Inc.

McKinney, K.A. et al. "Hormone Replacement Therapy and the Eye" *Journal of the British Menopause Society*, Mar. 2000, pp. 15-17, vol. 6, No. 1.

Milic, D. et al., "Structure and Reactivity of Steroidal Quinones", *J. Serb. Chem. Soc.*, 1997, pp. 755-768, vol. 62, No. 9.

Milic, D. et al., "The Synthesis and Biological Evaluation of A-Ring Substituted Steroidal *p*-Quinones", *Tetrahedron*, 1997, pp. 14073-14084, vol. 53, No. 41, Elsevier Science Ltd., Great Britain.

Milic, D. et al., "X-Ray Crystal Structure of 10β-Hydroxy-4β,5β-expoxyerstr-1-en-3,17-dione and Antitumor Activity of its Congeners", *Molecules*, 1999, pp. 338-352, vol. 4, MDPI.

Nilsen, J. and Brinton R., "Divergent impact of progesterone and medroxyprogesterone acetate (Provera) on nuclear mitogen-activated protein kinase signaling", *PNAS*, Sep. 2, 2003, pp. 10506-10511, vol. 100, No. 18.

Nilsen, J. and Brinton, R., "Impact of Progestins on Estrogen-Induced Neuroprotection: Synergy by Progesterone and 19-Norprogesterone and Antagonism by Medroxyprogesterone Aceate", *Endocrinology*, 2002, pp. 205-212, vol. 143, No. 1, The Endocrine Society, USA.

Numazawa, M. et al., "Oxygenation of 2,4-Dibromoestogens with Nitric Acid: A New Synthesis of 19-Nor Steroids", *Chem. Pharm Bull.*, 1989, pp. 2058-2062, vol. 37, No. 8, Pharmaceutical Society of Japan.

Ohe, T. et al., "Novel Metabolic Pathway of Estrone and 17β-Estradiol Catalyzed by Cytochrome P-450", *Drug Metabolism and Disposition*, 2000, pp. 110-112, vol. 28, No. 2, The American Society for Pharamcology and Experimental Therapeutics, USA.

Proaki-Tatrai, K. and Prokai, L., "Modifying peptide properties by prodrug design for enhanced transport into the CNS", *Progress in Drug Research*, 2003, pp. 155-188, vol. 61, Birkhäuser Verlag, Basel (Switzerland).

Prokai, L. et al. "Chemical Shield Mechanism for Estrogen Neuroprotection: Steroidal Quinols as new Molecular Leads" *Abstracts of Paper. At the National Meeting, American Chemical Society*, Mar. 23, 2003-Mar.27, 2003, vol. 225, No. 1/2.

Prokai, L. et al., "Quinol-based cyclic antioxidant mechanism in estrogen neuroprotein", *PNAS*, Sep. 30, 2003, pp. 11741-11746, vol. 100, No. 20.

Prokai, L. et al., "Short Communication: Quinol-Based Metabolic Cycle for Estrogen in Rat Liver Microsomes", *Drug Metabolism and Disposition*, 2003, pp. 701-704, vol. 31, No. 6, The American Society for Pharmacology and Experimental Therapeutics, USA.

Prokai, L. et al., "Synthesis and Biological Evaluation of 17β-Alkoxyestra-1,3,5(10)-trienes as Potential Neuroprotectants Against Oxidative Stress", *J. Med. Chem.*, 2001, pp. 110-114, vol. 44, American Chemical Society.

Prokai, L. et al., "Targeting Drugs to the Brain by Redox Chemical Delivery Systems", *Med. Res. Rev.*, 2000, pp. 367-416, vol. 20, No. 5, John Wiley & Sons, Inc.

Sedee, A.G. J. et al. (1983) "A sintesis for p-quinol compounds from phenols fused with other saturated rings" *Tetrahedron Letters* 24(51):5779-5780.

Solaja, B. et al., "A Novel *m*-CPBA Oxidation: *p*-Quinols and Epoxyquinols from Phenols", *Tetrahedron Letters*, 1996, pp. 3765-3768, vol. 37, No. 2kl1, Elsevier Science Ltd., Great Britain.

* cited by examiner a) R = COCH₃ (quinol acetate)

b) R = H (quinol)

R = H, alkyl (Me, Et) or substituted alkyl

QUINOL COMPOUND AND PHARMACEUTICAL COMPOSITION

CROSS-REFERENCE TO A RELATED APPLICATION

This application is a continuation application of application Ser. No. 11/682,072, filed Mar. 5, 2007 now abandoned; which is a continuation-in-part of application Ser. No. 10/731,528, filed Dec. 9, 2003, now U.S. Pat. No. 7,186,707; which claims the benefit of U.S. provisional patent application Ser. No. 60/432,354, filed Dec. 9, 2002. The subject application is also a continuation-in-part application of U.S. Ser. No. 10/405,413, filed Apr. 1, 2003; now U.S. Pat. No. 7,026,306; which claims the benefit of U.S. provisional patent application Ser. No. 60/369,589, filed Apr. 1, 2002. These applications are hereby incorporated by reference in their entirety, including all figures and tables.

GOVERNMENT SUPPORT

This invention was made with government support under a grant awarded from the National Institute of Neurological Disorders and Stroke under grant number NS44765, and a grant from the National Institutes of Health on Aging under grant number PO1 AG10485. The government has certain rights in the invention.

FIELD OF THE INVENTION

The present invention relates to prodrugs for use as ophthalmic agents, specifically for retinal protection. In particular, the present invention relates to the use of steroidal quinols as prodrugs of phenolic A-ring steroid compounds to treat and/or prevent eye pathologies.

BACKGROUND OF THE INVENTION

A variety of tissues metabolize estrogen (as a representative phenolic A-ring steroid) to various degrees. Of all of the tissues investigated, cornea appears to be the most active estrogen-metabolizing tissue (Stàrka, L and J Obenberger, "In vitro Estrone-Estradiol-17β Interconversion in the Cornea, Lens, Iris and Retina of the Rabbit Eye," *Arch Klin Exp Opthalmol*, 196:199-204 (1975)). Estrogens have demonstrated an important role in the health maintenance of all mucous membranes in the body, including the maintenance of a healthy ocular surface. Additional studies have revealed that the biological activity of estrogen may be effective in the protection and treatment of the eye, including the lens and retina, against cataracts and the detrimental effects of glaucoma.

Unfortunately, many regions of the eye are relatively inaccessible to systemically administered estrogens. For example, orally administered estrogen passes through the liver before reaching estrogen sensitive tissues. Because the liver contains enzymes that can inactivate the estrogen, the estrogen that eventually reaches tissue targeted for treatment is virtually ineffective. Moreover, systemic administration of estrogen often produces undesirable side effects, i.e., feminizing side effects in men.

As a result, topical drug delivery remains the preferred route of administration to the eye. There are a variety of factors that affect the absorption of drugs into the eye. These factors include: the instillation volume of the drug, the frequency of instilled drug administration, the structure and integrity of the cornea, the protein level in tears, the level of enzymes in tears, lacrimal drainage and tear turnover rate, as well the rate of adsorption and absorption of a drug by the conjunctiva, sclera, and eyelids.

Thus, the potential treatment of ocular disorders/conditions by estrogens or agents derived from estrogens is confounded by poor ocular bioavailability of pharmacologically active agents and by the likelihood of triggering systemic side effects associated with the administration of natural (endogenous) estrogens. The latter are due to absorption from the nasal cavity and the gastrointestinal (GI) tract after the topically administered estrogen hormone gains access to these pathways through its removal by the nasolacrimal apparatus of the eye. A potential way of reducing or even eliminating systemic side effects is to improve ocular targeting that would allow for the use of reduced doses of the biologically active agent in the ophthalmic drug formation.

Accordingly, the direct administration to an eye lens of estrogen having quinolines (i.e., 6-hydroxyquinoline) and fused quinolines that act as steroid receptor modulators to prevent or treat cataract disorders has been disclosed. In addition, the administration of 17-β-estradiol to the surface of the eye to alleviate dry-eye syndrome or keratoconjunctivitis sicca has been disclosed. Glycosides of catechol estrogens have been formulated that demonstrate antioxidant activity to the same degree as to that of the parent catechol estrogens. Nonetheless, all of the previously disclosed compounds and methods for applying estrogens to the eye relate to compounds that lack efficient corneal penetration and/or are inapplicable to men because of their activity as a female hormone.

As noted above, the major barrier to ocular drug penetration is the cornea. The cornea is composed of three layers: a lipid-rich epithelium, a lipid-poor soma, and a lipid-rich endothelium. Therefore, an agent must possess both lipophilic-hydrophilic balance for adequate transcorneal penetration and, thus, ocular bioavailability (Akers H J, "Ocular bioavailability of topically applied ophthalmic drugs," *Am Pharm*, NS23:33-36 (1983)). Thus, poor ocular bioavailability is an issue for estrogens and their synthetic analogs, because estrogens are highly lipid soluble molecules that are usually not amenable to adequate transcorneal penetration.

Prodrugs are inactive compounds that are converted in vivo into biologically active agents by enzymatic and/or chemical transformations. Prodrugs are advantageous because they can be designed to overcome problems associated with stability, toxicity, lack of specificity, or limited bioavailability, that may exist with the active form of a drug. Thus, there is a need to develop effective prodrugs of estrogen as a medical compound.

Estrogen quinols have been known for decades among organic chemists (Gold A. M., and Schwenk E., "Synthesis and reaction of steroidal quinols," *J Am Chem Soc*, 80:5683-5687 (1958)) though their metabolic formation has only been reported recently (Ohe T., et al., "Novel metabolic pathway of estrone and 17β-estradiol catalyzed by cytochrome P-450", *Drug Metab Dispos*, 28:11-112 (2000)). 10β-hydroxy-1,4-estradiene-3,7-dione and 10β,17β-dihydroxy-1,4-estradiene-3-one were detected from the respective estrogens during metabolic oxidation catalyzed by several cytochrome P-450 isoenzymes in rat liver microsomal systems. Contrary to well-known catechol metabolites of estrogens (Zhu, B. T. and Conney A. H., "Functional role of estrogen metabolism in target cells: review and perspective," *Carcinogenesis*, 19:1-27 (1998)), quinols do not possess an aromatic A-ring, making their biochemistry substantially different from that of catechols. Studies are currently underway to assess the nature of estrogen quinols.

BRIEF SUMMARY

The subject invention provides materials and methods wherein unique and advantageous steroidal quinols are used for a broad range of therapeutic purposes, including the treatment or prevention of ophthalmic disorders and/or conditions by modulating or activating estrogen receptors. These disorders and/or conditions include, but are not limited to, conjunctivitis, diabetic retinopathy, dry eye, glaucoma, and cataract.

A quinol (i.e., the 10α,β-hydroxyestra-1,4-diene-3-one structures) derived synthetically from phenolic A-ring steroids has been found to confer significant reduced lipid solubility compared to the parent phenolic A-ring steroid compounds to provide improved transcorneal penetration. Further, these quinols can be converted to phenolic A-ring steroid structures by endogeneous NAD(P)H as a reducing agent. In one embodiment, an oxidoreductase catalyst converts subject steroidal quinols to phenolic A-ring steroids that possess pharmacological activity in the eye. The present invention exploits the benefits of prodrugs (including but not exclusively based on the quinol structure as a novel promoiety) for phenolic A-ring steroid compounds to provide ocular bioavailability of the therapeutic agent in question. Prodrugs are, by definition, inactive compounds that are converted to the biologically active agents by chemical or enzymatic transformation in vivo.

The subject invention provides a mechanism by which quinol derived phenolic A-ring steroid compounds confer beneficial ophthalmic effects. The subject compounds possess a lipophilic-hydrophilic balance for transcorneal penetration and are readily reduced into parent phenolic A-ring steroid compounds to provide protection or treatment against various ocular symptoms and disorders. The compounds according to the subject invention appear to be highly advantageous as prodrugs to provide protection and/or treatment against ocular disorders. These prodrugs confer low lipid solubility and are readily converted by endogenous reducing agents into active phenolic A-ring steroid compounds. To the extent that these prodrugs have reduced feminizing effects and systemic toxicity, they would be expected to be quite advantageous for protecting or treating the eye against ocular disorders such as cataract or glaucoma.

In a specific embodiment, the subject invention provides steroidal quinol compounds that are, themselves, inactive. However, these quinol structures can act as prodrugs because they are converted to a therapeutically active phenolic A-ring steroid upon exposure to a reducing agent. Additionally, because an active phenolic A-ring steroid compound arises after conversion by a reducing agent, a smaller concentration of the steroidal quinols is required as compared to direct administration of phenolic A-ring steroid, thus reducing the potential for systemic toxicity.

In one particular embodiment of the subject invention, isomers of 10-hydroxyestra-1,4-diene-3-one quinol structure (estrone-quinol) are converted to active, phenolic A-ring steroid compounds (i.e., estrone) when exposed to a reducing agent. In related embodiments, quinols are derived from estrogen analogues, i.e., 3,17-dihydroxyestra-1,3,5(10),9(11)-tetraene (ZYC1); 2-(1-adamantyl)-estra-1,3,5(10)-triene-3,17β-diol; and 2-(1-adamantyl)-10β,17β-dihydroxyestra-1,4-dien-3-one.

In another embodiment, steroidal quinols are provided as prodrugs that require at least one-step activation in vivo to yield pharmaceutically active estrogen compounds. In a related embodiment, quinols derived from estrogen prodrugs that require two-step activation can include a polar functional group to enhance hydrophilicity at the 17-OH group or may have the 10-OH group esterified to decrease lipophilicity through phosphate, or N,N,N-trialkylammonium esters.

In another embodiment, the 3,17-keto groups of quinols of the present invention can be functionalized as oxime and/or alkoximes. In doing so, preliminary compounds to the subject quinols are created (to form i.e. pro-prodrugs). Such functionalized quinols (i.e., 3-keto functionalized as an oxime) can be used for a variety of therapeutic purposes, including use for ocular-specific delivery of phenolic A-ring steroids.

An object of the present invention is to provide compounds formulated for ophthalmic administration. For example, solutions or suspensions of these compounds may be formulated in the form of eye drops, or membranous ocular patch, which is applied directly to the surface of the eye.

It is another object of the subject invention to provide an ophthalmic agent with an increased therapeutic index associated with treatments using the subject compounds disclosed herein.

DETAILED DISCLOSURE

Figure 1:
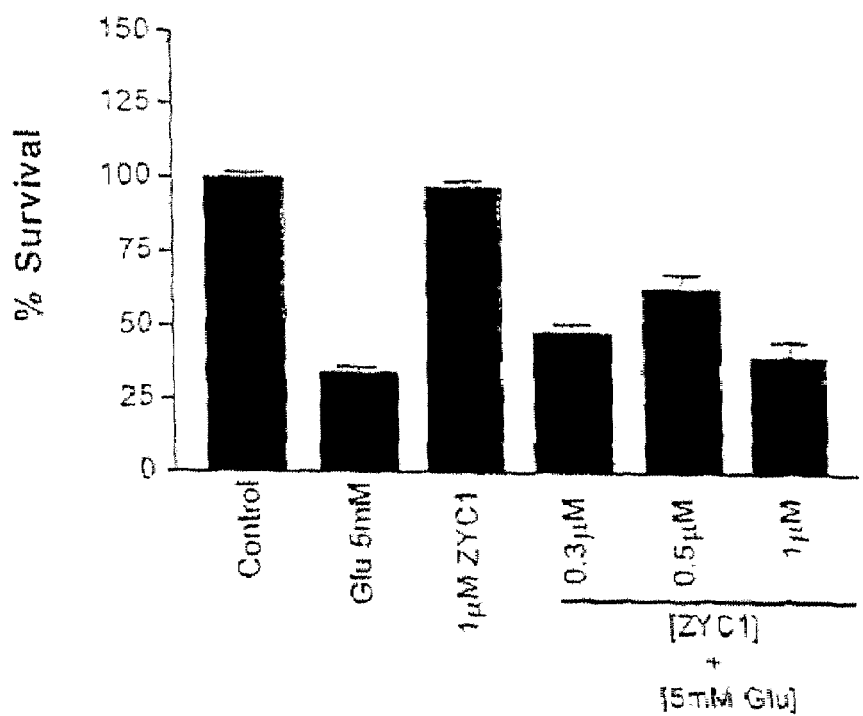
FIG. 1 illustrates the viability of retinal ganglial cells in the presence of glutamate, estrogen analog 3,17-dihydroxyestra-1,3,5(10),9(11)-tetraene (ZYC1), or combinations of glutamate and various concentrations of ZYC1.

The subject invention provides steroidal quinol compounds that produce phenolic A-ring steroids in vivo. In one embodiment, these compounds provide improved physicochemical properties including, but not limited to, favorable ocular bioavailability and facile transcorneal penetration. In a preferred embodiment, estrogen derived quinol compounds demonstrate decreased lipophilicity as compared to lipophilic estrogens and estrogen analogues.

In another embodiment of this invention, these compounds treat and/or protect against various ocular diseases. Preferred compounds of the subject invention are effective in treating and/or preventing maladies associated with vision-threatening intraocular damage due to pathophysiological predispositions. Particularly preferred compounds are those which treat glaucoma and/or macular degeneration.

In a specific embodiment, the subject invention provides steroidal quinol compounds that are, themselves, inactive.

However, these quinol structures can act as prodrugs because they are converted to a therapeutically active phenolic A-ring steroid upon exposure to a reducing agent. Additionally, because an active phenolic A-ring steroid compound arises after conversion by a reducing agent, a smaller concentration of the steroidal quinols is required due to their improved ocular bioavailability as compared to direct administration of estrogen, thus reducing the potential for systemic toxicity. In a related embodiment of the subject invention, steroidal quinols are provided as prodrugs that are converted into an active phenolic A-ring steroid via a one-step conversion by a reducing agent. Suitable reducing agents include endogenous NAD(P)H or oxidoreductases.

In one particular embodiment of the subject invention, a 10β-hydroxyestra-1,4-diene-3-one quinol structure (estrone-quinol) is converted to an active, phenolic A-ring estrogen compound (estrone) when exposed to a reducing agent. In related embodiments, quinols are derived from estrogen analogues, i.e., 3,17-dihydroxyestra-1,3,5(10),9(11)-tetraene (ZYC1); 2-(1-Adamantyl)estrone (ZYC3); 2-(1-Adamantyl)-estra-1,3,5(10)-triene-3,17 β-diol; and 2-(1-Adamantyl)-10β,17β-dihydroxyestra-1,4-dien-3-one.

In another embodiment, steroidal quinols are provided as prodrugs that require two (or more than two) step activation in vivo to yield pharmaceutically active estrogen compounds. The liberation of a parent estrogen occurs through a two-step reaction: (1) enzymatic (phosphatase, esterase) cleavage of the ester group followed by (2) spontaneous and fast chemical conversion of a quinol by an endogenous reducing agent. In a related embodiment, these compounds according to the present invention can include a polar functional group to enhance hydrophilicity at the 17-OH group or may have the 10-OH group esterified to decrease lipophilicity through phosphate or N,N,N-trialkylammonium esters (such as 2-(1-adamantyl)-estra-1,3,5(10)-triene-3,17β-diol and 2-(1-adamantyl)-10β,17β-dihydroxyestra-1,4-dien-3-one).

In another embodiment, the prodrugs according to the subject invention can be synthesized by attaching a polar functional group to enhance affinity to water and facilitate the transport of the prodrug of the subject invention through the lipid-poor middle stroma in the cornea. In a preferred embodiment, the 17-OH group of a quinol according to the subject invention is the primary site to which a polar functional group is added. In another preferred embodiment, the 10β-OH of a steroidal quinol (i.e., 17-hydroxyestra-1,4-diene-17-one) is blocked by esterification to make the resultant prodrug more lipophilic than the phenolic A-ring steroid derived quinol.

It will be noted that the structure of some of the compounds of this invention includes asymmetric carbon atoms. It is to be understood accordingly that the isomers arising from such asymmetry (i.e., all enantiomers and diastereomers) are included within the scope of this invention, unless indicated otherwise. Such isomers can be obtained in substantially pure form by conventional methods including, for example, by classical separation techniques and by stereochemically controlled synthesis.

Definitions

A number of terms are used herein to designate particular elements of the present invention. When so used, the following meanings are intended:

The term "estrogen," as used herein, refers to both naturally occurring and synthetic substances classed as estrogen on the basis of their therapeutic or biological action (see listing under 'Estrogens' in the 'Therapeutic Category and Biological Activity Index' of The Merck Index, 12th Edition, Merck Research Laboratories, NJ, 1996, page THER-22). According to this listing, estrogens may be steroids (i.e., estradiol, ethinyl estradiol, colpormon, conjugated estrogenic hormones, equilenin, equilin, estriol, estrone, mestranol, moxestrol, mytatrienediol, quinestradiol and quinestrol) or non-steroids (i.e., diethylstilbestrol, dienestrol, benzestrol, broparoestrol, chlorotrianisene, dimestrol, fosfestrol, hexestrol, methallenestril, methestrol). Additional substances known to be estrogenic, that is, they interact with cellular estrogen receptors and mimic the effects of estrogens, include estrogenic substances that have been shown to be tissue selective in their estrogenic effects. Diverse classes of molecules fall within this category, for example: quinolines and fused quinolines that act as steroid receptor modulators such as 3,9-dihydroxy-5H-benzofuro[3,2-c]quinoline-6-one and those disclosed in WO 96/19458; phytoestrogens which occur naturally in plants such as forage plants, soya beans, seeds, berries and nuts (Jordan et al., "Structure-activity relationships of estrogen," Env. Health Per., 61:97-110 (1985)), including isoflavones such as genistein and genistein glycosides, equol, O-desmethyl-angolensin, biochanin A, daidzein and formononetin; flavones such as phloretin, 4'-6-dihydroxyflavone and tricin, and coumestans such as coumestrol, 4'-O-methyl coumestrol, medicagol and sativol, lignans such as mataresinol, enterodiol, enterolactone, guaiaretic acid, nordihydroguaiaretic acid and derivatives thereof, β-sitosterol; mycoestrogens such as zeranol, zearalenol and zearalenone; estrogen receptor agonist/antagonists, such as tamoxifen, hydroxytamoxifen, zindoxifene and its metabolites, nafoxidene and derivatives, clomiphene, centchroman, benzothiophenes and related compounds such as benzothiophene-derived LY139478 (Eli Lilly), raloxifene and droloxifene, which may mimic the action of estrogens in certain types of cells, while opposing it in others (Raisz, L. G., "Estrogen and bone: new pieces to the puzzle," Nature. Med., 2(10):1077-8 (1996)); and many para-substituted phenols that contain a strategically located phenolic hydroxyl not impaired by an alkyl substitution (see Jordan et al., "Structure-activity relationships of estrogen," Env. Health Per., 61:97-110 (1985)), including octyl phenyl, nonyl phenol, butylated hydroxyanisole, bisphenol A and trihydroxy-8-prenylflavone. Note that estrogenic substances in this general category may also be referred to in the literature as 'estrogens' (see Jordan et al., 1985, for example). As already described above (for 'estrogens' as defined in Merck), estrogenic substances may exert their estrogenic effect(s) directly or they may require metabolic conversion to an active form after administration. For example, metabolic activation of some phytoestrogens involves demethylation to phenols (Jordan et al., "Structure-activity relationships of estrogen," Env. Health Per., 61:97-110 (1985)).

The term "estrogen derived quinols," (i.e., 10α/β-hydroxyestra-1,4-diene-3-one structure) as used herein, refers to quinols and quinol derivatives related to estrogens, as described above, and para-substituted phenols obtained by oxidation of the phenolic ring, as described below.

The term "phenolic A-ring steroid" used herein refers to compounds containing a 3-hydroxy-1,3,5(10)-triene moiety as the six-membered A-ring of a steroid, steroid analogue or steroid mimic, including compounds that manifest affinity to estrogen receptors (i.e., 3,17-dihydroxyestra-1,3,5(10),9(11)-tetraene) as well as compounds that do not bind to such receptors (i.e., 2-(1-adamantyl)-3-hydroxyestra-1,3,5 (10)-trien-17-one).

The term "steroidal quinol" used herein refers to a steroid containing a 10α/β-hydroxy-1,4-diene-3-one moiety as the six-membered A-ring of a steroid, steroid analogue or steroid mimic.

The term "ophthalmic disorders," and/or "ophthalmic conditions," as used herein, refers to ophthalmic diseases, conditions, and/or disorders including, without limitation, those associated with the anterior chamber of the eye (i.e., hyphema, synechia); the choroid (i.e., choroidal detachment, choroidal melanoma, multifocal choroidopathy syndromes); the conjunctiva (i.e., conjunctivitis, cicatricial pemphigoid, filtering Bleb complications, conjunctival melanoma, Pharyngoconjunctival Fever, pterygium, conjunctival squamous cell carcinoma); connective tissue disorders (i.e., ankylosing spondylitis, pseudoxanthoma elasticum, corneal abrasion or edema, limbal dermoid, crystalline dystrophy keratits, keratoconjunctivitis, keratoconus, keratopathy, megalocomea, corneal ulcer); dermatologic disorders (i.e., ecrodermatitis enteropathica, atopic dermatitis, ocular rosacea, psoriasis, Stevens-Johnson syndrome); endocrine disorders (i.e., pituitary apoplexy); extraocular disorders (i.e., Abducens Nerve Palsy, Brown syndrome, Duane syndrome, esotropia, exotropia, oculomotor nerve palsy); genetic disorders (i.e., albinism, Down syndrome, Peters Anomaly); the globe (i.e., anopthalmos, endophthalmitis); hematologic and cardiovascular disorders (i.e., Giant Cell Arteritis, hypertension, leukemias, Ocular Ischemic syndrome, sickle cell disease); infectious diseases (i.e., actinomycosis, botulism, HIV, diphtheria, *Escherichia coli*, Tuberculosis, ocular manifestations of syphilis); intraocular pressure (i.e., glaucoma, ocular hypotony, Posner-Schlossman syndrome), the iris and ciliary body (i.e., aniridia, iris prolaps, juvenile xanthogranuloma, ciliary body melanoma, iris melanoma, uveitis); the lacrimal system (i.e., alacrima, Dry Eye syndrome, lacrimal gland tumors); the lens (i.e., cataract, ectopia lentis, intraocular lens decentration or dislocation); the lid (i.e., blepharitis, dermatochalasis, distichiasis, ectropion, eyelid coloboma, Floppy Eye syndrome, trichiasis, xanthelasma); metabolic disorders (i.e., gout, hyperlipoproteinemia, Oculocerebrorenal syndrome); neurologic disorders (i.e., Bell Palsy, diplopia, multiple sclerosis); general opthalmologic (i.e., red eye, cataracts, macular degeneration, red eye, macular degeneration); the optic nerve (i.e., miningioma, optic neuritis, optic neuropathy, papilledema); the orbit (i.e., orbital cellulits, orbital dermoid, orbital tumors); phakomatoses (i.e., ataxia-telangiectasia, neurofibromatosis-1); presbyopia; the pupil (i.e., anisocoria, Horner syndrome); refractive disorders (i.e., astigmatism, hyperopia, myopia); the retina (i.e., Coats disease, Eales disease, macular edema, retinitis, retinopathy); and the sclera (i.e., episcleritis, scleritis).

The term "patient," as used herein, describes an organism, including mammals, to which treatment with the compositions according to the present invention is provided. Mammalian species that benefit from the disclosed methods of treatment include, and are not limited to, apes, chimpanzees, orangutans, humans, monkeys; and domesticated animals (i.e., pets) such as dogs, cats, mice, rats, guinea pigs, and hamsters.

The term "polar aprotic solvent" refers to polar organic solvents lacking an easily removed proton, including, but not limited to, ethyl acetate, dimethylformamide (DMF), and acetonitrile.

The term "pharmaceutically acceptable salts," as used herein, refers to those carboxylate salts, esters, and prodrugs of the compound of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention.

Pharmaceutically acceptable salts are well known in the art and refer to the relatively non-toxic, inorganic and organic acid addition salts of the compound of the present invention. For example, S. M. Berge, et al. describe pharmaceutically acceptable salts in detail in *J. Pharmaceutical Sciences*, 66:1-19 (1977) which is incorporated herein by reference. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

The term "pharmaceutically acceptable prodrugs," as used herein, refers to those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention.

The term "prodrug," as used herein, refers to a derivative of a biologically active compound (i.e., the steroidal quinols according to the present invention) that lacks pharmaceutical activity, but is converted (i.e., by NAD(P)H) to an active agent, which is a phenolic A-ring steroid such as estrogen hormone, estrogen analogue, substituted estrogen or estrogen-receptor agonist or antagonist) upon interaction with a biological or chemical system, for example catalyzed reduction by enzymes in the eye. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference. A prodrug, according to the present invention, can be converted into an active compound with one or more steps.

The term "substituted" shall be deemed to include multiple degrees of substitution by a named substituent. Where multiple substituent moieties are disclosed, the substituted compound can be independently substituted by one or more of the disclosed or claimed substituent moieties, singly or severally.

Unless otherwise specified, as used herein, the term "alkyl" refers to a straight or branched or cyclic alkyl moiety. In one embodiment, the alkyl moiety is $C_{1-20}$ alkyl, which refers to an alkyl moiety having from one to twenty carbon atoms, including for example, methyl, ethyl, propyl, isopropyl, butyl, tert-butyl, pentyl, hexyl and octyl, cycloalkyl including for example cyclopropyl, cyclobutyl, cyclopentyl, cyclohexyl. The alkyl group specifically includes fluorinated alkyls such as $CF_3$ and other halogenated alkyls such as $CH_2CF_2$, $CF_2CF_3$, the chloro analogs, and the like. The alkyl group can be optionally substituted with one or more moieties selected from the group consisting of aryl, heteroaryl, heterocyclic, carbocycle, alkoxy, heterocycloxy, heterocylalkoxy, aryloxy; arylalkoxy; heteroaryloxy; heteroarylalkoxy, carbohydrate, amino acid, amino acid esters, amino acid amides, alditol, halo, haloalkyl, hydroxyl, carboxyl, acyl, acyloxy, amino, amido, alkylamino, dialkylamino, arylamino, nitro, cyano, thiol, imide, sulfonic acid, sulfate, sulfonyl, sulfanyl, sulfinyl, sulfamoyl, carboxylic ester, carboxylic acid, amide, phosphonyl, phosphinyl, phosphoryl, thioester, thioether, oxime, hydrazine, carbamate, phosphonic acid, phosphate, phosphonate, phosphinate, sulfonamido, carboxamido, hydroxamic acid, sulfonylimide, substituted or unsubstituted urea connected through nitrogen; or any other desired functional group that does not inhibit the pharmacological activity of this compound, either unprotected, or protected as necessary, as known to those skilled in the art, for example, as taught in Greene, et al., Protective Groups in Organic Synthesis, John Wiley and Sons, Second Edition, 1991, hereby incorporated by reference.

The term "alkenyl" refers to a straight or branched alkyl moiety having one or more carbon double bonds, of either E or Z stereochemistry where applicable. This term includes for example, vinyl, 1-propenyl, 1- and 2-butenyl, and 2-methyl-2-propenyl, as well as "cycloalkenyl" groups such as cyclopentenyl and cyclohexenyl.

The term "alkoxy," as used herein, and unless otherwise specified, refers to a moiety of the structure —O-alkyl, wherein alkyl is as defined above. The alkyl group can be optionally substituted as described above. Alkoxy groups can include $OCF_3$, $OCH_2CF_3$, $OCF_2CF_3$, and the like.

The term alkynyl refers to a hydrocarbon with at least one triple bond, including for example, $C_1$ to $C_{10}$ groups including but not limited to ethynyl, 1-propynyl, 1- and 2-butynyl, 1-methyl-2-butynyl, and the like.

The term "aryl," as used herein, and unless otherwise specified, refers to phenyl, biphenyl, or naphthyl, and preferably phenyl. The aryl group can be optionally substituted with one or more of the moieties selected from the group consisting of alkyl, heteroaryl, heterocyclic, carbocycle, alkoxy, aryloxy, aryloxy; arylalkoxy; heteroaryloxy; heteroarylalkoxy, carbohydrate, amino acid, amino acid esters, amino acid amides, alditol, halo, haloalkyl, hydroxyl, carboxyl, acyl, acyloxy, amino, amido, alkylamino, dialkylamino, arylamino, nitro, cyano, thiol, imide, sulfonic acid, sulfate, sulfonyl, sulfanyl, sulfinyl, sulfamoyl, carboxylic ester, carboxylic acid, amide, phosphonyl, phosphinyl, phosphoryl, thioester, thioether, oxime, hydrazine, carbamate, phosphonic acid, phosphate, phosphonate, phosphinate, sulfonamido, carboxamido, hydroxamic acid, sulfonylimide or any other desired functional group that does not inhibit the pharmacological activity of this compound, either unprotected, or protected as necessary, as known to those skilled in the art, for example, as taught in Greene, et al., "Protective Groups in Organic Synthesis," John Wiley and Sons, Second Edition, 1991. Alternatively, adjacent groups on the aryl ring may combine to form a 5 to 7 membered carbocyclic, aryl, heteroaryl or heterocyclic ring.

The term "aralkoxy" refers to an aryl group attached to an alkyl group that is attached to the molecule through an oxygen atom. The aryl and alkyl groups can be optionally substituted as described above.

The term "aralkyl," as used herein, and unless otherwise specified, refers to an aryl group as defined above linked to the molecule through an alkyl group as defined above. The aryl and alkyl portions can be optionally substituted as described above.

The term "aryloxy," as used herein, refers to an aryl group bound to the molecule through an oxygen atom. The aryl group can be optionally substituted as set out above for aryl groups. The terms "heteroaryl" and "heteroaromatic," as used herein, refer to monocyclic or bicyclic aromatic ring systems of five to ten atoms of which at least one atom is selected from O, N, and S, in which a carbon or nitrogen atom is the point of attachment, and in which one additional carbon atom is optionally replaced with a heteroatom selected from O or S, and in which from 1 to 3 additional carbon atoms are replaced by nitrogen heteroatoms.

Heteroaryl thus includes aromatic and partially aromatic groups that contain one or more heteroatoms. Examples of this type include but are not limited to are furan, benzofuran, thiophene, benzothiophene, pyrrole, pyrazole, imidazole, oxazole, benzoxazole, thiazole, benzthiazole, isothiazole, thiadiazole, triazole, benzotriazole, furazan, benzofurazan, thiafurazan, benzothiafurazan, tetrazole, oxadiazole, triazine, pyridine, pyridazine, pyrimidine, pyrazine, triazine, indolizine, indole, isoindole, purine, quinoline, benzimidazole, pteridine, isoquinoline, cinnoline, quinazoline, and quinoxaline.

The term "heteroaralkyl," as used herein, and unless otherwise specified, refers to a heteroaryl group as defined above linked to the molecule through an alkyl group as defined above.

The term "heterocyclealkyl," as used herein, refers to a heterocyclic group bound to the molecule through an alkyl group. The heterocyclic group and the alkyl group can be optionally substituted as described above. The term "heterocycloalkyl" can also refer to a saturated heterocyclic moiety having from two to six carbon atoms and one or more heteroatom from the group N, O, and S (or oxidized versions thereof) which may be optionally benzofused at any available position. This includes, for example, azetidinyl, pyrrolidinyl, tetrahydrofuranyl, piperidinyl, benzodioxolyl and the like. The term "heterocycloalkyl" also refers to an alicyclic moiety having from three to six carbon atoms and one or more heteroatoms from the group N, O, and S and having in addition one double bond. Such moieties may also be referred to as "heterocycloalkenyl" and includes, for example, dihydropyranyl, and the like.

The term "heterocyclic" refers to a nonaromatic cyclic group that may be partially (contains at least one double bond) or fully saturated and wherein there is at least one heteroatom, such as oxygen, sulfur, nitrogen, or phosphorus in the ring. The term heteroaryl or heteroaromatic, as used herein, refers to an aromatic that includes at least one sulfur, oxygen, nitrogen or phosphorus in the aromatic ring. Non-limiting examples of heterocyclics and heteroaromatics are pyrrolidinyl, tetrahydrofuryl, piperazinyl, piperidinyl, morpholino, thiomorpholino, tetrahydropyranyl, imidazolyl, pyrolinyl, pyrazolinyl, indolinyl, dioxolanyl, 1,4-dioxanyl, aziridinyl, furyl, furanyl, pyridyl, pyrimidinyl, benzoxazolyl, 1,2,4-oxadiazolyl, 1,3,4-oxadiazolyl, 1,3,4-thiadiazole, indazolyl, 1,3,5-triazinyl, thienyl, isothiazolyl, imidazolyl, tetrazolyl, pyrazinyl, benzofuranyl, quinolyl, isoquinolyl, benzothienyl, isobenzofuryl, pyrazolyl, indolyl, isoindolyl, benzimidazolyl, purinyl, carbazolyl, oxazolyl, thiazolyl, benzothiazolyl, isothiazolyl, 1,2,4-thiadiazolyl, isooxazolyl, pyrrolyl, quinazolinyl, cinnolinyl, phthalazinyl, xanthinyl, hypoxanthinyl, pyrazole, imidazole, 1,2,3-triazole, 1,2,4-triazole, 1,2,3-oxadiazole, thiazine, pyridazine, or pteridinyl wherein a heteroaryl or heterocyclic group can be optionally substituted with one or more substituent selected from the same substituents as set out above for aryl groups. Functional oxygen and nitrogen groups on the heteroaryl group can be protected as necessary or desired. Suitable protecting groups can include trimethylsilyl, dimethylhexylsilyl, t-butyldimethylsilyl, and t-butyldiphenylsilyl, trityl or substituted trityl, alkyl groups, acyl groups such as acetyl and propionyl, methanesulfonyl, and p-toluenelsulfonyl.

The term "heteroaryloxy," as used herein, refers to a heteroaryl group bound to the molecule through an oxygen atom. The heteroaryl group can be optionally substituted as set out above for aryl groups.

The term "heterocyclearalkoxy" refers to a heterocyclic group attached to an aryl group attached to an alkyl-O— group. The heterocyclic, aryl and alkyl groups can be optionally substituted as described above.

The term "electrolyte," as used herein, refers to salts generally and specifically to ions. An electrolyte refers to an ion that is electrically-charged, either negative or positive. Common electrolytes include chloride ($Cl^-$), bromide ($Br^-$), bicarbonate ($HCO_3^-$), sulfate ($SO_4^{2-}$), sodium ($Na^+$), potassium ($K^+$), calcium ($Ca^{2+}$), and magnesium ($Mg^{2+}$).

Abbreviations

Abbreviations used in the examples are: DCC for 1,3-dicyclohexylcarbodiimide; DMAP for 4-dimethylamino-pyridine; LC/MS for liquid chromatography-mass spectrometer; m-CPBA for meta-chloroperoxybenzoic acid; and PhMe/EtOAC for toluene/ethyl acetate.

Steroidal Quinols

In one embodiment, a quinol of Formula I is provided as follows

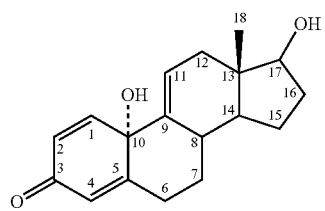

or a pharmaceutically acceptable salt or prodrug thereof; wherein the quinol of Formula I is derived from the following estrogen analogue (ZYC1):

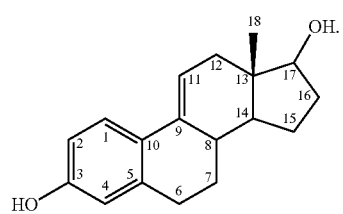

ZYC1 is an analogue of estrogen and has been demonstrated to have estrogen-like activity. The physicochemical properties of ZYC1 inhibit facile transcorneal penetration upon topical administration (i.e., eye-drops). In accordance with the present invention, ZYC1 is oxidized to produce an steroidal quinol, 10,17-dihydroxyestra-1,4,9(11)-triene-3-one ("ZYC1-quinol"). The ZYC1-quinol, as discussed in more detail below, has demonstrated improved physicochemical properties, including decreased lipophilicity, to facilitate transcorneal penetration.

In another embodiment, a quinol of Formula II is provided as follows:

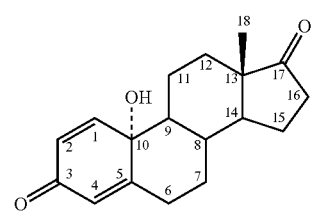

or a pharmaceutically acceptable salt or prodrug thereof, wherein the quinol of Formula II is derived from 3-hydroxyestra-1,3,5(10-triene-17-one (estrone).

In yet another embodiment, a quinol of Formula III is provided as follows:

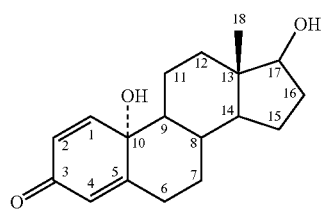

III or a pharmaceutically acceptable or prodrug thereof, wherein the quinol of Formula III is derived from 3,17-dihydroxyestra-1,3,5(10)-triene (estradiol).

The compounds of Formulas I-III can also be functionalized at the 3- or 17-keto group as an oxime or alkoxime. Such compounds are useful as preliminary compounds to the quinol, for use as pro-prodrug compounds. These compounds would be useful for a variety of therapeutic purposes including, for example, use as a β-blocker.

The compounds and processes of the invention will be better understood in connection with the Examples, which are intended as an illustration of and not a limitation upon the scope of the invention.

EXAMPLE 1

Physicochemical Properties of ZYC1

Human retinal ganglial cells (RGC) were incubated with glutamate (5 mM), the estrogen analogue 3,17-dihydroxyestra-1,3,5(10),9(11)-tetraene (ZYC1) or combination of glutamate and various concentrations of ZYC1. As illustrated in FIG. 1, glutamate killed about 70% of RGC while the compound of Formula ZYC1 alone had no effect on RGC viability. In the presence of all three concentrations of ZYC1, glutamate killed significantly fewer cells.

Figure 2:
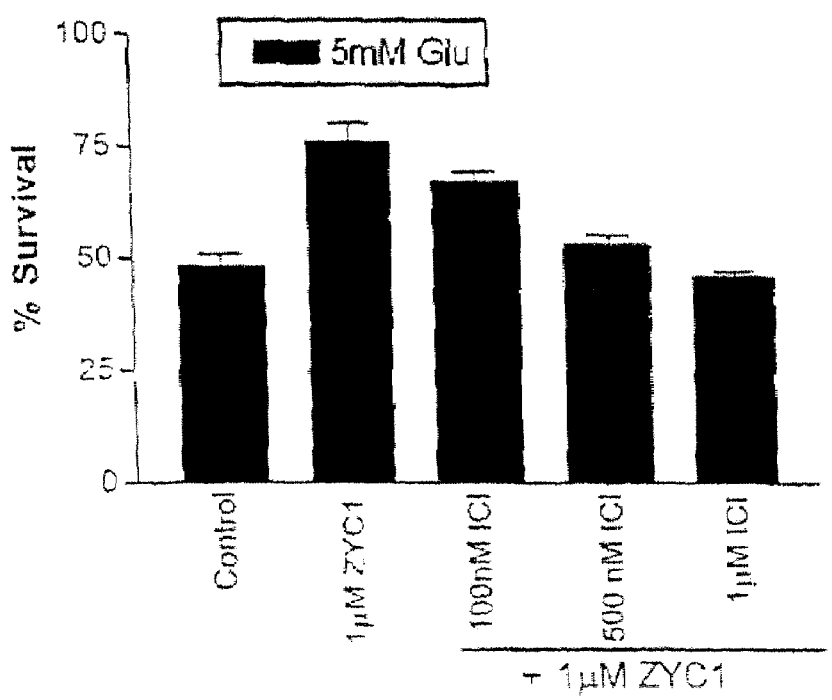
FIG. 2 illustrates retinal ganglial cell viability when treated with glutamate in the presence or absence of ZYC1 or ZYC1 incubated in the presence of various concentrations of estrogen receptor antagonist, ICI182,780 (ICI).

RGC were treated with glutamate (5 mM) in the presence or absence of ZYC1. As illustrated in FIG. 2, this estrogen analogue, ZYC1, reduced the number of RGC killed by glutamate. Where ZYC1 was incubated in the presence of various concentrations of estrogen receptor antagonist, IC1182,780 (ICI) (which at the lowest concentration used, was more than 100-times its IC50), little antagonism of ZYC1 protection of RGC was seen. This data suggests that ZYC1 protects RGC through a non-estrogen receptor mediated mechanism. However, the physicochemical properties of ZYC1 permit negligible transcorneal penetration upon topical administration.

EXAMPLE 2

Improved Physicochemical Properties of Steroidal Quinols

To test the hypothesis that directed modification of an estrogen improves physicochemical properties of transcorneal penetration, estrone was used as a lead compound. The following Table I indicates a very significant drop in lipophilicity of Formula I, Formula II, and Formula III, compared to the parent phenolic A-ring steroids, ZYC1, estrone, and estradiol. The log of the n-octanol/water partitioning coefficient (log P or log $D_{7.4}$) is the measure of attraction to lipid phase versus an aqueous phase. Log P is a crucial factor governing passive membrane partitioning, influencing permeability opposite to its effect on solubility (i.e., increasing log P enhances permeability while reducing water solubility). Thus, the results of Table I demonstrate that the lipophilic-hydrophilic balance of Formula I, Formula II, and Formula III are closer to the ideal value for facile transcorneal penetration and favorable bioavailability than the parent phenolic A-ring steroids, ZYC1, ZYC3, estrone, and estradiol. It has been demonstrated that the ideal log P value for the brain is approximately 2. Though an ideal log P value for the cornea has not yet been determined, a log P value of two should be a reasonable value for the cornea.

TABLE I

| COMPOUND | Log P | P |
|---|---|---|
| 3-hydroxyestra-1,3,5(10)-triene-17-one (estrone) | 4.54 | 64,670 |
| 3,17β-dihydroxyestra-1,3,5(10)-triene (estradiol) | 4.01 | 10,230 |
| 3,17-dihydroxyestra-1,3,5(10),9(11)-tetraene (ZYC1) | 3.57 | 3,715 |
| 2-(1-adamantyl)-3-hydroxyestra-1,3,5(10)-trien-17-one [2-(1-adamantyl)estrone] (ZYC3) | 6.83 | $6.76 \cdot 10^6$ |
| 10β-hydroxyestra-1,4-diene-3,17-dione ("estrone quinol") | 2.20 | 158 |
| 10β,17β-dihydroxyestra-1,4-diene-3-one ("estradiol quinol") | 1.67 | 47 |
| 10β,17-dihydroxyestra-1,4,9(11)-triene-3-one ("Formula * quinol") | 1.30 | 20 |
| 2-(1-adamantyl)-10β-hydroxyestra-1,4-diene-3,17-dione ["2-(1-adamantyl)estrone quinol"] ( | 4.30 | 19,953 |

The log P values pertain to n-octanol/water partitioning were predicted by the method incorporated into CAChe WorkSystem Pro 5.0 (Fujitsu America, Inc., Beaverton, Oreg.).

EXAMPLE 3

General Methods for Preparing a Steroidal Quinol

By way of example, Formula II (estrone quinol; 10β-hydroxyestra-1,4-diene-3,17-dione) was prepared by the following Scheme I:

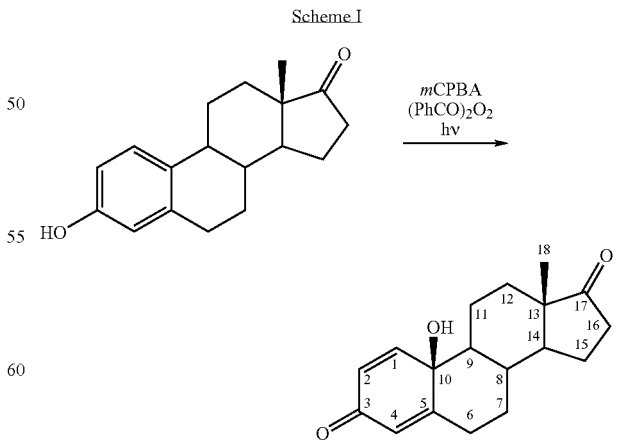

As understood by the skilled artisan, steroidal quinols according to the present invention may be synthesized using a "one-pot" phenol to quinol transformation. The synthesis method utilizes m-CPBA as an oxidant, dibenzoyl peroxide [(PheCO)$_2$O$_2$] as a radical initiator and visible-light irradiation that, in refluxing aprotic solvent, produces excellent yields of the quinols of the present invention.

By way of example, Solaja et al., *Tetrahedron Letters*, 37:21, 3765-3768 (1996) discloses a "one-pot" method for synthesizing estrone-quinol. Oxidation of estrone to synthesize 10β-hydroxyestra-1,4-diene-3,17-dione is performed by heating a stirred solution of estrone (10.00 g, 37.0 mmol), m-CPBA (22.53 g, 111.0 mmol; 85% Jansen Chimica), and (PheCO)$_2$O$_2$ (900 mg, 3.70 mmol) in 2 L mixture of CCl$_4$/Me$_2$CO (4/1) to reflux for 3 hours while irradiated with a 60 Watt tungsten lamp. Upon evaporation of the solvent, extraction is performed with CHCl$_3$ (3×200 mL), washing with NaHCO$_3$ (2×100 mL) and H$_2$O (100 mL), and drying over anhydrous Na$_2$SO$_4$. The residue is then chromatographed on SiO$_2$ column. Elution may be performed with PhMe/EtOAc (1/1 and 7/3, respectively) and crystallization from benzene produces 5.19 g (49%) of estrone quinol as colorless needles.

Data regarding the resulting estrone quinols, as observed by Solaja et al. are as follows: mp=219-221° C. (benzene); $^1$H-NMR (250 MHz, DMSO-d$_6$): 7.13 (d, j=10.4 Hz, H—C (1)), 6.07 (dd, J=10.4, 2.4 Hz, H—C(2)), 5.92 (irreg. T, J$_{4,2}$=2.4, J$_{4,6\beta}$=1.2 Hz, H—C(4)), 5.67 (s, H-o, exchangeable with D$_2$O), 2.67 (tdd, J=15.2, 6.4, 1.2 Hz, H$_\beta$—C(6)), 1.97-1.83 (m, H$_\beta$—C(8) and H$_\beta$—C(11)), 1.30-1.18 (m, H$_\alpha$—C(11)), 0.97 (s, H$_3$C—C(13)); $^{13}$C NMR (62.9 MHz, DMSO-d$_6$): 220.33 (C(17)), 185,53 (C(3)), 165.09 (C(5)), 150.25 (C(1)), 128.30 (C(2)), 123.09 (C(4)), 70.10 (C(10)), 51.18 (C(( )), 50.10 (C(14)), 47.75 (C(13)), 35.62 (C(16)), 34.58 (C(8)), 32.19 (C(7)), 31.80 (C(6)), 31.03 (C(11)), 22.00 (C(12)), 21.90 (C(15)), 13.73 (C(18)); MS (EI, m/z): 286(M$^+$, 84), 268(M$^+$-H$_2$O, 39), 150(68), 145(100), 124(75), 107(50), 91(50), 79(54), and 55(60).

Alternatively, estrome quinols of the present invention can be prepared using 2-(1-adamantyl)-3-hydroxyestra-1,3,5 (10)-trien-17-one [2-(1-adamantyl)estrone], which can be made using methods previously described by Lunn, W. H. and E. Farkas, "The adamantly carbonium ion as a dehydrogenating agent, its reactions with estrone," *Tetrahedron*, 24:6773-6776 (1968). Estrone (270 mg, 1 mmol) and 1-adamantanol (170 mg, 1 mmol) were added to anhydrous n-pentane (6 mL) and the stirred mixture was cooled with an ice bath. Boron trifluoride etherate (BF$_3$ EtOEt, 0.4 mL) was added over a 10 minutes period. After an additional 15 min, the ice bath was removed and stirring was continued for an additional 45 min at room temperature. During the 45 min, the solid present in the reaction mixture was dissolved and yellow oil formed. Crushed ice was then added while shaking and swirling the reaction flask and pink solid was formed. The filtered crude pink product was washed with water until the filtrate had a neutral pH and the solid was dried in a vacuum oven at 50° C. The pink crude powder (0.4 g) was purified by flash chromatography (silica gel, eluted with 20% ethyl acetate in hexanes to yield the pure product; 0.31 g, 76.7%). The product was recrystallized from a mixture of chloroform and isopropyl alcohol and had: mp 322-324° C., lit mp 295-296° C.; $^1$H NMR (CDCl$_3$, 300 MHz) δ 0.91 (s, 3H, C$_{18}$—CH$_3$), 2.8 (m, 2H, C$_6$—CH$_2$), 4.71 (s, 1H, C$_3$—OH), 6.42 (s, 1H, Aromatic H), 7.15 (s, 1H, Aromatic H).

Figure 3:
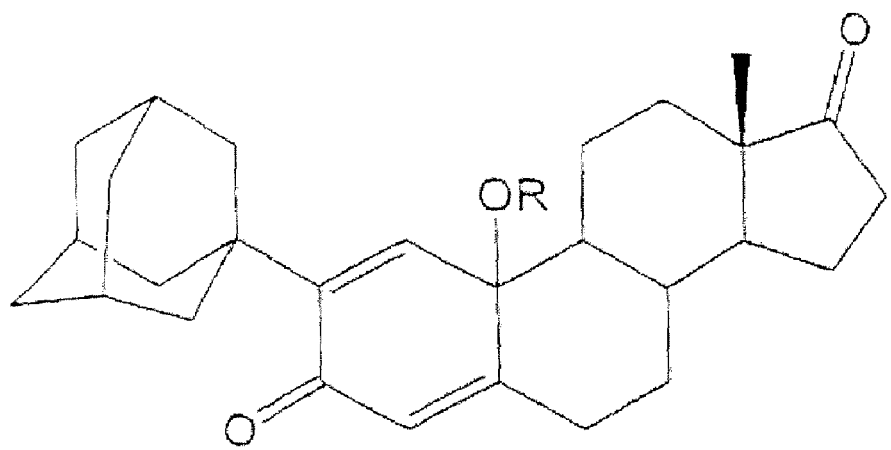
FIG. 3 illustrates a quinol acetate in accordance with the subject invention.

2-(1-Adamantyl)estrone (also referred to herein as ZYC3) was oxidized with lead-acetate to the corresponding quinol acetate using the following procedures. To a solution of 3 g 2-(1-adamantyl)estrone in 50 ml of glacial acetic acid 11 g of lead(IV)-acetate was added. The solution was stirred at room temperature for 1 day. Then, the solution was concentrated in vacuo to an oil that was treated with 50 ml of water and 50 ml of chloroform. The organic layer was separated and washed with 10% NaHCO$_3$ and water. After drying over Na$_2$SO$_4$ the chloroform was removed and the residue was purified by column chromatography on silica gel using hexane ethyl acetate 4:1 (v/v) eluent. The pure quinol acetate (as illustrated in FIG. 3), which is also a potential prodrug, has R$_f$=0.5 on silicagel TLC with the same eluent. Typical resonances (ppm) in $^1$H-NMR (CDCl$_3$) spectrum indicating the conversion to 2-substituted estrone quinol acetate were observed: 6.4 (s, 1H, H-1); 6.0 (s, 1H, H-4); 2.0 (s, 3H, 10-acetyl).

The quinol acetate (was then hydrolyzed to the quinol (where R=H; prepared as described above) in methanol using a slight excess of NaOMe in methanol (25% w/v) overnight at room temperature. Then the solution was concentrated and glacial acetic acid was added to adjust the pH slightly acidic. Upon adding water the quinol precipitated out as a pale yellow solid that was again purified by column chromatography the same way as its acetate (R$_f$=0.53). Typical resonances (ppm) in $^1$H-NMR (CDCl$_3$) indicating the conversion to 2-substituted estrone quinol were observed: 6.6 (s, 1H, H-1); 5.9 (s, 1H, H-4). MS (EI): m/z 420 (M$^{+•}$).

Figure 4:
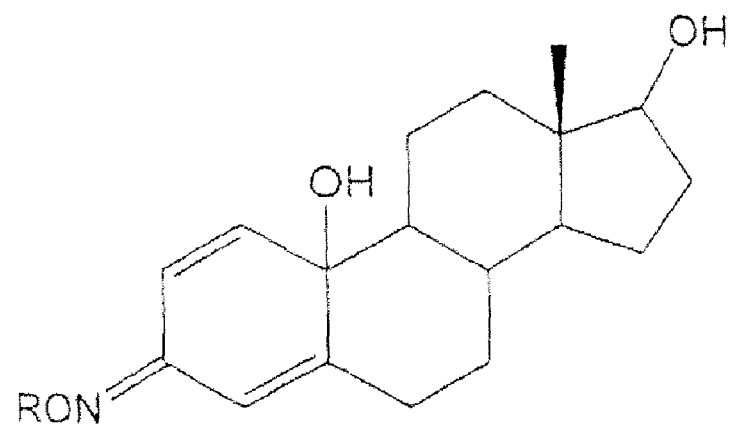
FIG. 4 illustrates an (alk)oxime of a quinol, in accordance with the subject invention.

To prepare (alk)oxime estradiol quinols of the subject invention, such as those illustrated in FIG. 4, 0.5 g of hydroxylamine hydrochloride is added to 0.5 g of estradiol quinol or alkoxyamine hydrochloride) in 5 ml of ethanol, 0.5 ml of pyridine was added and the solution was refluxed overnight. After cooling, the ethanol was removed and ice-cold water was added. The mixture was stirred until the oxime crystallized.

EXAMPLE 4

Physicochemical Properties of ZYC3

Figure 5:
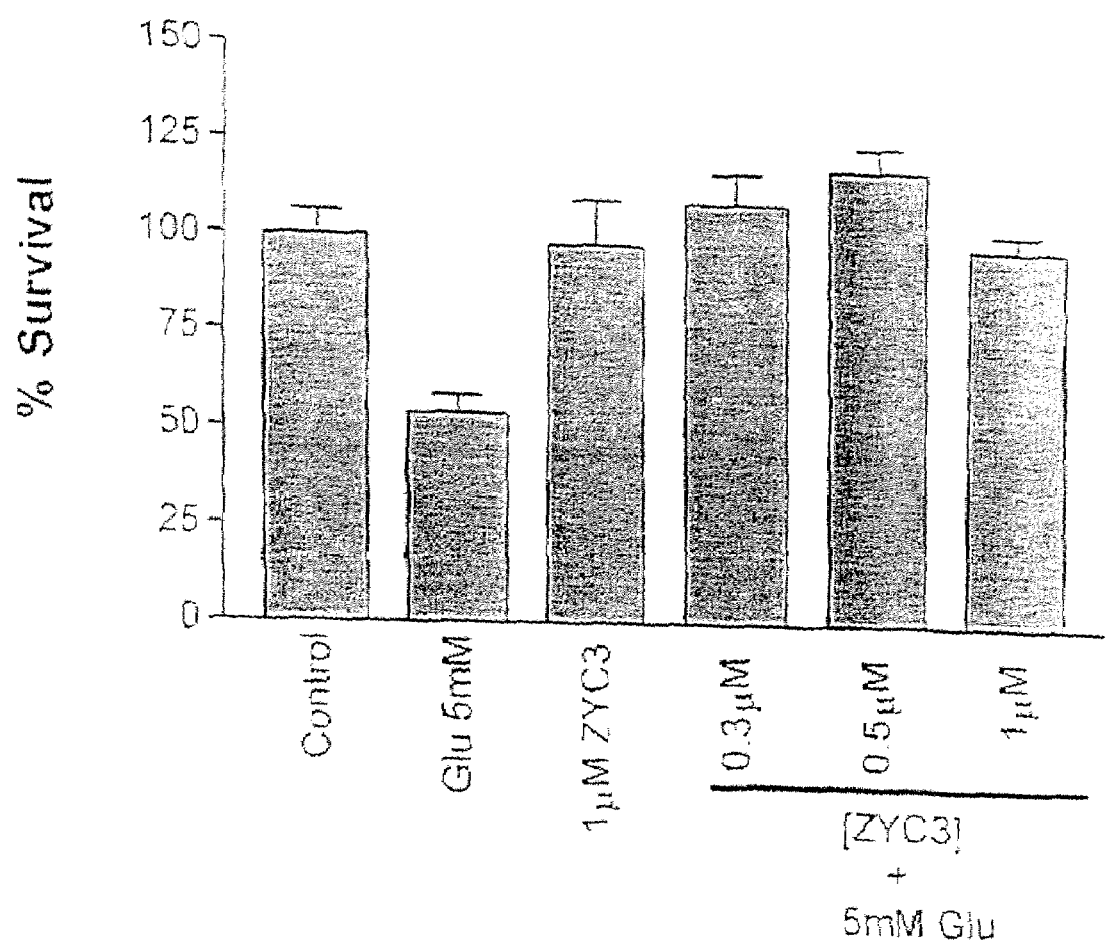
FIG. 5 illustrates the viability of retinal ganglial cells in the presence of glutamate, phenolic A-ring steroid 2-(1-adamantyl)-3-hydroxyestra-1,3,5 (10)-trien-17-one (ZYC3), or combinations of glutamate and various concentrations of ZYC3.

RGC were incubated with glutamate (5 mM), with 2-(1-adamantyl)-3-hydroxyestra-1,3,5 (10)-trien-17-one (ZYC3), or with a combination of glutamate and various concentrations of ZYC3. As illustrated in FIG. 5, glutamate killed about 70% of RGC while the compound of ZYC3 alone has no affect on RGC viability. In the presence of three different concentrations of ZYC3, glutamate killed significantly fewer cells (No statistically significant difference from RGC survival without exposure to glutamate).

EXAMPLE 5

Prodrug Activity

Figure 6:
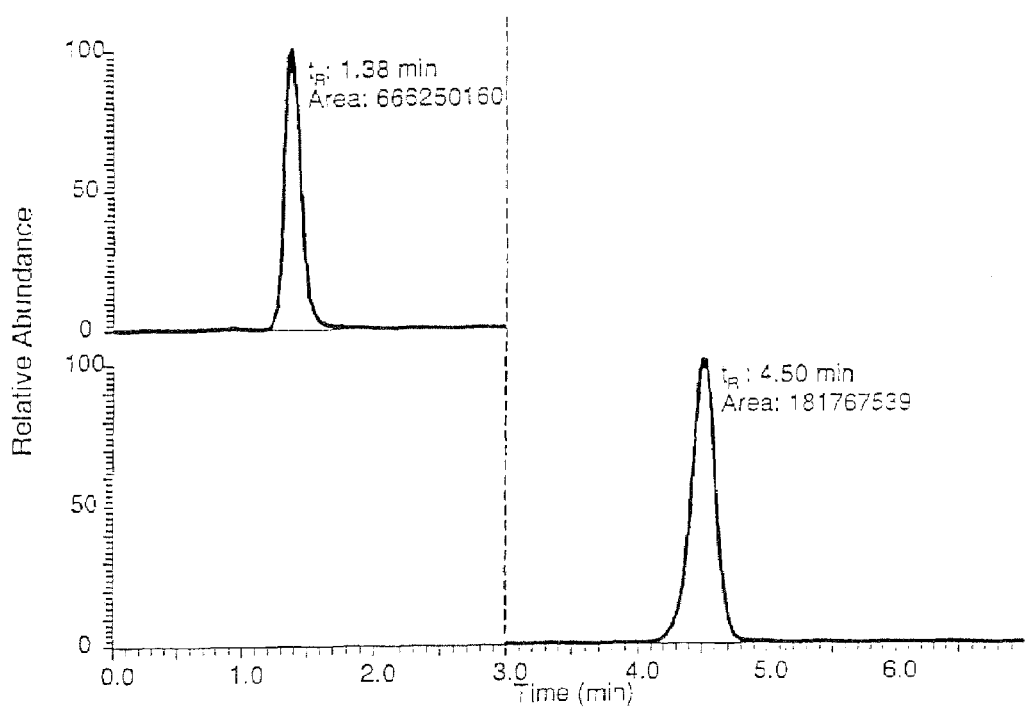
FIG. 6 illustrates LC/MS/MS analysis demonstrating the detection of 10β-hydroxyestra-1,4-dien-3,17-dione (estrone-quinol, $t_R$=1.38) and a product formed from it ($t_R$=4.5 min.) after the incubation of estrone-quinol with NADPH.
Figure 7:
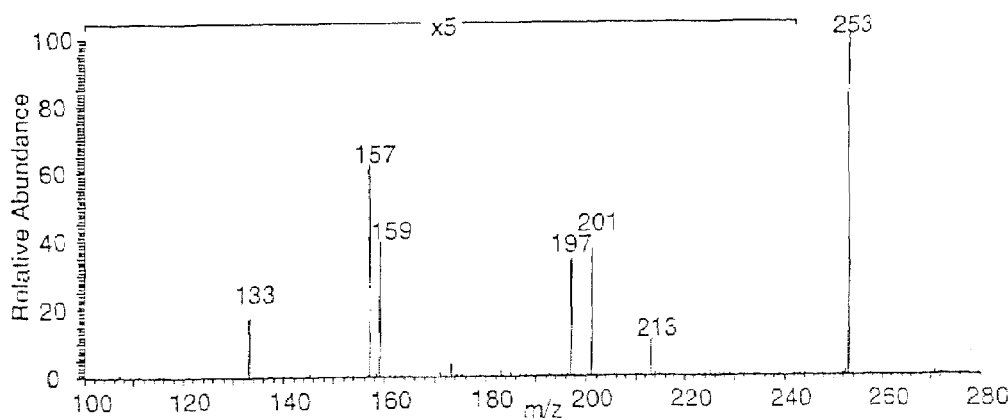
FIG. 7 illustrates MS/MS analysis of the chromatographic peak at $t_R$=4.5 min., which is identical to that of estrone.
Figure 8:
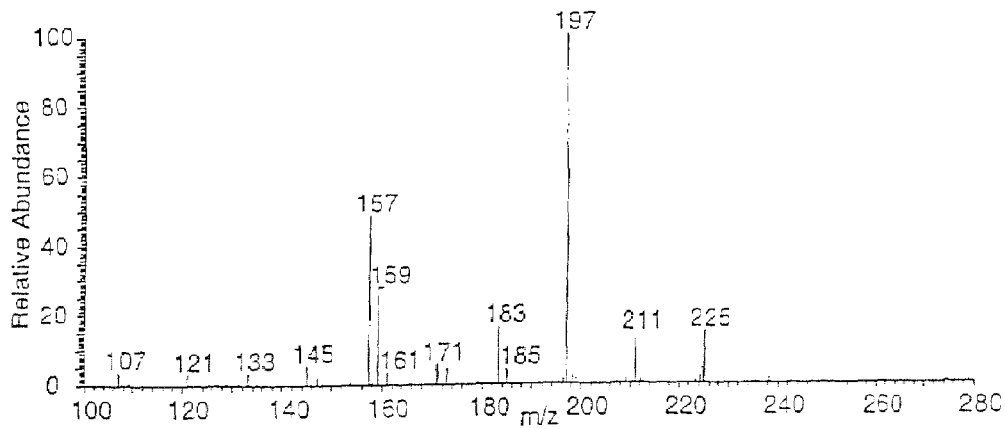
FIG. 8 illustrates $MS^3$ recording from the chromatographic peak, $t_R$=4.5 min., m/z 253 selected as precursor after MS/MS, which is identical to that of estrone.

By way of example, conversion of Formula II by NAD(P)H as an endogenous reducing agent was tested. Estrone quinol (0.1 mM) and 1.0 mM of NADPH or NADH in 0.1M sodium phosphate buffer (1 ml final volume, pH 7.5) was incubated at 37° C. At incremental time points, 100 μl aliquots were removed into ice-cold centrifuge tubes, and 100 μl of glacial acetic acid was added. After immediate extraction with ethyl acetate, the organic layer was evaporated under nitrogen stream. Reconstitution of the samples with the liquid chromatography mobile phase was followed by LC/MS analyses, the results of which are illustrated in FIGS. 6-8. For the control experiment, no reducing agent was used.

Liquid chromatography separation was done using a Supelco (Bellfonte, Pa.) 5 cm×2.1 mm i.d. Discovery HS C-18 reversed-phase column with 0.25 ml/min water:methanol:2-propanol:acetic acid:dichloromethane (53:35:5:5:2, v/v) as a mobile phase. The sample residues were dissolved in 40 μl of mobile phase, respectively, and 5 μl of the solution was injected for analysis. Mass spectra were recorded on a quadruple ion-trap instrument (LCQ®, ThermoFinnigan, San Jose, Calif.) using positive-ion atmospheric-pressure chemical ionization (APCI) as the method of ionization. MS/MS and MS³ product-ion scans were obtained after collision-induced dissociation (CID) with helium as the target gas. Comparison with authentic reference compound (retention time, $t_R$, and mass spectra) was used for unambiguous identification of estrone. As an internal standard, 1,3,5(10)-estratrien-17α-ethynyl-17β-ol was added before each sample extraction. Estrone and estrone quinol levels were determined by LC/APCI-MS/MS and calibration with solutions of known concentrations of estrone (0.02 μM to 11 μM) and estrone quinol (0.2 μM to 125 μM) extracted for analyses. The chromatographic peak areas for estrone and estrone quinol were obtained from m/z 271→253 and m/z 287→269 MS/MS transitions, respectively. Formation of estrone was clearly detectable even after a short period of time, when the incubation was carried out in the presence of NADH and, especially, NADPH.

The rate of conversion at 37° C. and with a 10-fold access of the ubiquitous reducing agent NADPH is $6.0 \times 10^{-7} \pm 4 \times 10^{-8}$ M·min$^{-1}$, which indicates a rapid process required for the proposed action of a quinol as a prodrug. Enzymes may also catalyze reductions in the eye. See Sichi H and D. W. Nebert, "In: Extrahepatic Metabolism of Drugs and Other Foreign Compounds (Gram T E, Ed.)," S.P. Medical and Scientific Books, New York, pp. 333-363 (1980), and Starka L and J. Obenberger. (In vitro estrone-estradiol-17beta interconversion in cornea, lens, iris and retina of rabbit eye," *Arch Klin Exp Opthalmol*, 196:199-204 (1975).

EXAMPLE 6

General Methods for Preparing Prodrugs

In general, where a steroidal quinol according to the subject invention contains a hydroxyl group (i.e., 17-OH group or 10β-OH group), an "ester" moiety can replace the hydroxyl portion to form a non-acidic (neutral) ester compound. The addition of a polar functional group (i.e., tertiary amide or phosphate ester) enhances the phenolic A-ring steroid-derived quinol's affinity to water and thus facilitates the transport of the quinol through the lipid-poor soma in the cornea. The following compounds of Formula III, Formula IIIa and Formula IIIb, illustrate polar functional groups attached at the 17-OH group.

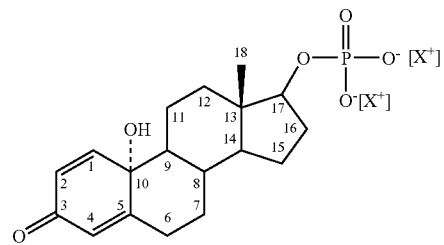

wherein each R and R' is independently hydrogen, alkyl, alkenyl, alkynyl, alkoxy, aryl, aralkoxy, aralkyl, aryloxy, hydroxyalkyl, alkoxyalkyl, heteroaralkyl, heterocyclealkyl, heteroaryloxy; and heterocyclearalkoxy;

X is an electrolyte; and n is an integer from 1 to 20.

By way of example, a prodrug of Formula I (n=1, R=H) may be obtained by converting Formula III into an ester compound as illustrated in the following Scheme IIa. To a solution of 10β,17β-dihydroxyestra-1,4-diene-3one (Formula I, estradiol quinol) in chloroform or ethyl acetate bromoacetic anhydride, DCC, and DMAP are added. The resulting mixture is stirred at 20-25° C. for 48 hours. The organic solution is extracted with water then dried over Na2SO4 and evaporated. The residue is purified by chromatography (silica gel: Aldrich, Merck grade 60, 230-400 mesh, 32×2 cm; elution with hexane containing gradually increasing concentrations of ethyl acetate from 0 to 6%). The purified residue in hexane is then placed in a closed system under argon, and trimethylamine (gas) was added at 20-25° C. then the precipitate was filtered, and rinsed with hexane. The resultant prodrug of estradiol quinol (10β,17β-dihydroxyestra-1,4-diene-3-one-17-acetyl-trimethylammonium bromide) should have adequate solubility and sufficient stability to allow for formulation and storage. Further, the exemplary prodrug of estrone quinol is easily converted through an enzymatic or chemical process to the active compound, estrone, within the body, preferably the eye. In the following Scheme IIa, a prodrug of Formula I can be obtained.

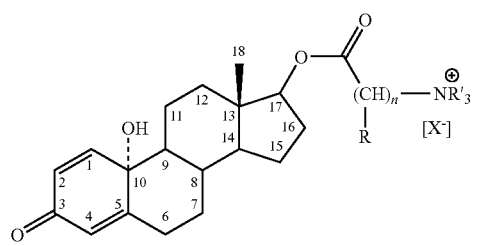

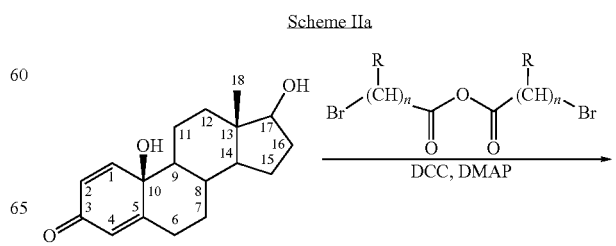

-continued

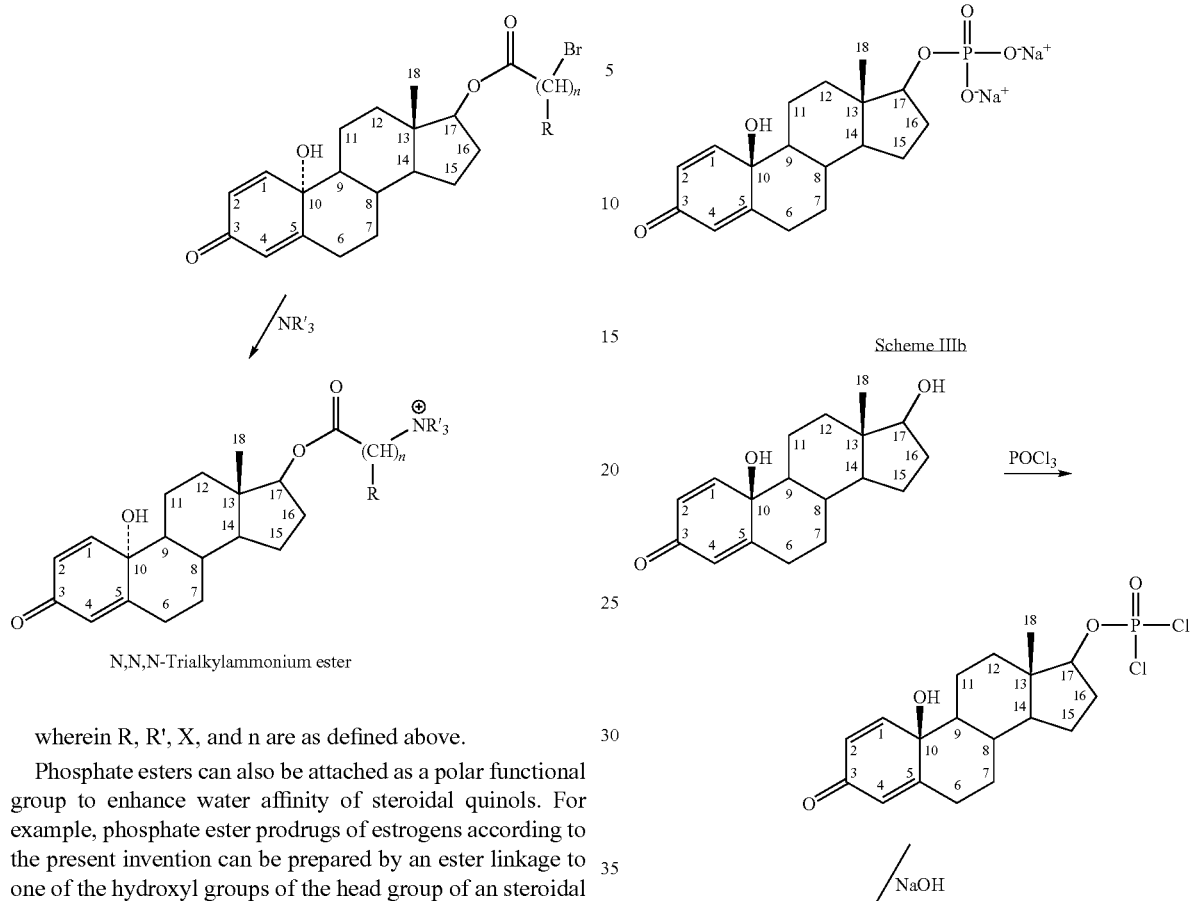

Scheme IIIb wherein R, R', X, and n are as defined above.

Phosphate esters can also be attached as a polar functional group to enhance water affinity of steroidal quinols. For example, phosphate ester prodrugs of estrogens according to the present invention can be prepared by an ester linkage to one of the hydroxyl groups of the head group of an steroidal quinol.

By way of example, the prodrug of estradiol, in accordance with the present invention, may be prepared using general methods as depicted in the following Schemes IIIa and IIIb.

Scheme IIIa

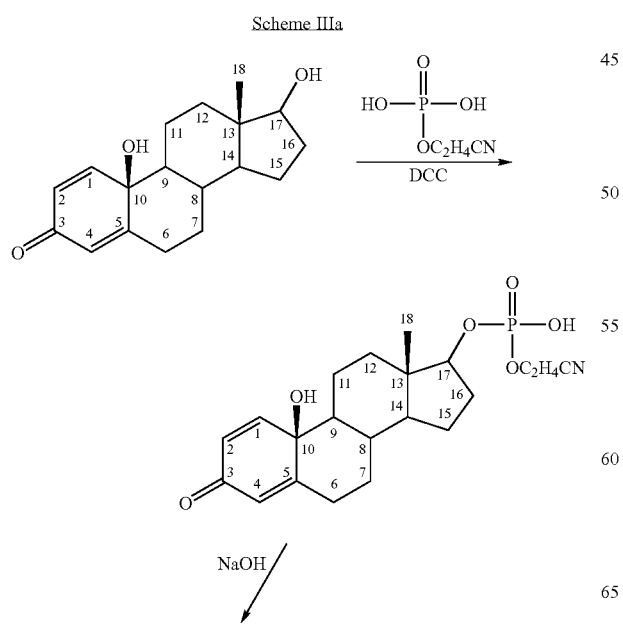

EXAMPLE 7

Physicochemical Properties of 2-(1-adamantyl)-estra-1,3,5(10)-triene-3,17β-diol as compared with 2-(1-adamantyl)-3-hydroxyestra-1,3,5 (10)-trien-17-one (ZYC3)

Because lipid peroxidation (LPO) is a common marker of damage induced by reactive oxygen species (ROS) (Gutteridge J M C, "Lipid-peroxidation and antioxidants as biomarkers of tissue-damage," *Clin Chem*, 41: 1819-1828 (1995); Kaur and Geetha, "Screening methods for antioxidants—A review," *Mini-Rev Med Chem*, 6: 305-312 (2006)), two assays were employed to measure capacity to inhibit LPO: the ferric thiocyanate (FTC) and the thiobarbituric acid reactive substances (TBARS) methods. With these assays, the autoxidation of linoleic acid (a lipid model) is measured in the absence and, then, presence of different concentration of antioxidants. The FTC method measures the amount of peroxide in initial stages of lipid oxidation (Kikuzaki H and Nakatani N., "Antioxidant effects of some ginger constituents," *J Food Sci,* 58: 1407-1410 (1993)). During the oxidation process, peroxide is gradually decomposed to lower molecular-weight compounds such as malondialdehyde (MDA) that is measured by the TBARS method (Kikuzaki and Nakatani, *J Food Sci,* 58: 1407-1410 (1993)). Therefore, the FTC and TBARS assays are complementary, when they are used to evaluate antioxidants for their capacity to inhibit LPO.

The FTC assay is based on the oxidation of ferrous to ferric ion by the lipid hydroperoxides (LOOH), followed by a subsequent complexation of $Fe^{3+}$ with the thiocyanate anion (Mihaljevic B A, Katusin-Razem B and Razem D, "The reevaluation of the ferric thiocyanate assay for lipid hydroperoxides with special considerations of the mechanistic aspects of the response." *Free Rad Biol Med,* 21: 53-63 (1996)). The amount of lipid hydroperoxides is measured spectrophotometrically as ferric thiocyanate complex, which gives a strong absorbance at 500 nm.

The TBARS assay is a widely adopted and sensitive method for measurement of lipid peroxidation (Callaway J K, Beart P M and Jarrott B. "A reliable procedure for comparison of antioxidants in rat brain homogenates." *J Pharmacol Toxicol Meth,* 39: 155-162 (1998)). The oxidation of unsaturated fatty acids leads to the formation of MDA as a breakdown product (Mihaljevic et al., *Free Rad Biol Med,* 21: 53-63 (1996)). The reaction of MDA with thiobarbituric acid (TBA) produces a pink chromogen when heated at low pH with a typical maximum absorbance at 532 nm (Esterbauer H and Cheeseman K H. "Determination of aldehydic lipid peroxidation products: malondialdehyde and 4-hydroxynonenal." *Methods Enzymol,* 186: 407-421 (1990)). The MDA-TBA complex measured by the TBARs assay is a gauge of LOOH formation (Janero D R. "Malondialdehyde and thiobarbituric acid-reactivity as diagnostic indices of lipid peroxidation and peroxidative tissue injury." *Free Rad Biol Med,* 9: 515-540 (1990)). Inhibitions were calculated from absorbances measured in the presence of the compounds at different concentrations and absorbance of the control reaction (no antioxidant added), and $IC_{50}$ values (concentration that inhibits 50% of lipid peroxidation) were determined by sigmoidal fitting (Prizm 3.0, GraphPad) of the inhibition versus concentration curves. A smaller $IC_{50}$ value represents a higher potency to inhibit LPO. Both the FTC and TBARS methods were utilized to assess the differences between 2-(1-adamantyl)-estra-1,3,5(10)-triene-3,17β-diol and 2-(1-adamantyl)-3-hydroxyestra-1,3,5(10)-trien-17-one (ZYC3). The results, as illustrated in Table 2 below, indicate that 2-(1-adamantyl)-estra-1,3,5(10)-triene-3,17β-diol has higher potency than ZYC3 to inhibit lipid peroxidation.

TABLE 2

| Compound | $IC_{50}$: FTC method (μM) | $IC_{50}$: TBARS method (μM) |
|---|---|---|
| 2-(1-adamantyl)-3-hydroxyestra-1,3,5(10)-trien-17-one | 5.3 ± 1.2 | 5.8 ± 1.3 |
| 2-(1-adamantyl)-estra-1,3,5(10)-triene-3,17β-diol | 1.5 ± 0.1 | 0.75 ± 0.11 |

EXAMPLE 8

2-(1-adamantyl)-10β,17β-dihydroxyestra-1,4-dien-3-one Prodrug Activity

As illustrated below in Scheme IV, 2-(1-Adamantyl)-$\Delta^1$-dehydro-19-nortestosterone (also referred to herein as 2-(1-adamantyl)-10β,17β-dihydroxyestra-1,4-dien-3-one) is a prodrug of 2-(1-adamantyl)-estra-1,3,5(10)-triene-3,17β-diol.

Scheme IV

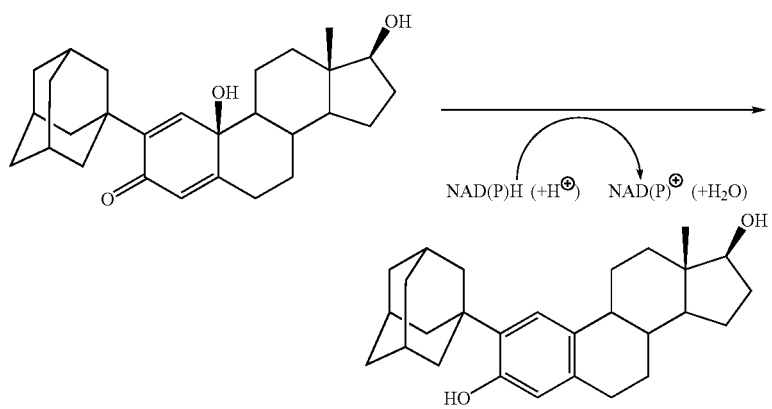

Experiments conducted on 2-(1-adamantyl)-$\Delta^1$-dehydro-19-nortestosterone indicate that it is highly suitable for pharmaceutical purposes (beneficial properties exhibited such as permeability across biological membranes if released from non-erodible drug delivery systems such as ocular inserts or polymeric nanoparticles, and the like). As indicated in Table 3 below, the lipophilicity property of the 2-(1-adamantyl)-$\Delta^1$-dehydro-19-nortestosterone prodrug is preferred to that of the converted, active compound: 2-(1-adamantyl)-estra-1,3,5(10)-triene-3,17β-diol:

TABLE 3

| Compound | $logP_{calc}^{a,(i)}$ | $logP_{exp}^{a,(ii)}$ |
|---|---|---|
| 2-(1-adamantyl)-estra-1,3,5(10)-triene-3,17β-diol | 6.40 | 6.51 |

TABLE 3-continued

| Compound | logP$_{calc}$[a,(i)] | logP$_{exp}$[a,(ii)] |
|---|---|---|
| 2-(1-adamantyl)-Δ$^1$-dehydro-19-nortestosterone | 3.81 | 3.26 |

[a]P denotes the n-octanol/water partitioning coefficient, which is a measure of attraction to lipid phase versus an aqueous phase. The logarithm of n-octanol/water partitioning coefficients (logP) was
(i)calculated from molecular model by the method incorporated into the program BioMedCAChe (version 6.1, Fujitsu America, Inc., Beaverton, OR) and
(ii)measured experimentally by the shake-flask method (Leo A, Hansch C, and Elkins D. "Partition coefficients and their uses." Chem. Rev, 71: 525-616. (1971)).

EXAMPLE 9

General Methods for Preparing 2-(1-adamantyl)-Δ$^1$-dehydro-19-nortestosterone Prodrug Scheme V below illustrates a method for synthesizing 2-(1-adamantyl)-Δ$^1$-dehydro-19-nortestosterone:

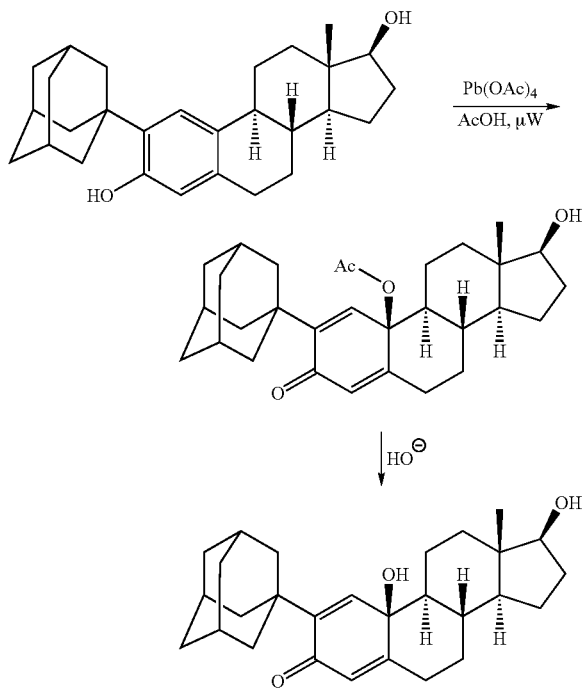

The synthesis method of Scheme V is based on microwave-assisted oxidation of the corresponding phenolic compounds with lead (IV) acetate. The corresponding phenolic compound is prepared according to Lunn & Farkas (Tetrahedron 24, 6773-6776, 1968). Briefly, 17β-estradiol (1 mmol) and 1-adamantanol (1.05 mmol) was added to 20 ml dry hexane and followed by the drop wise addition of 0.5 ml of BF$_3$·Et$_2$O under ice cooling. The cooling was, then, removed and the stirring continued overnight. The reaction mixture was poured onto crashed ice and the obtained precipitate was filtered off, washed with water and dried. Column chromatographic purification was done on silicagel, using hexane:ethyl acetate 4:1 (v/v) eluent. (White solid: m.p. 180-182° C.) APCI-MS: (M+H)$^+$m/z 407. Conversion of the phenolic compound to 2-(1-adamantyl)-Δ$^1$-dehydro-10β-hydroxy-19-nortestosterone was done by microwave-accelerated oxidation with lead(IV) acetate. The phenolic compound (1 mmol) was dissolved in 6 mol glacial acetic acid and lead (IV) acetate (1.7 mmol) was added. The closed-vessel reaction under pressure control was performed in a glass vessel (capacity 10 mL) sealed with a septum. A CEM (Matthews, N.C.) Discover monomode microwave apparatus, operating at a frequency of 2.45 GHz with continuous irradiation power from 0 to 300 W was used. The temperature was measured by infrared detection with continuous feedback temperature control, and maintained at a constant value by power modulation. The reaction temperature was set at 45° C. After irradiation for 25 min, the reaction vessel was cooled rapidly to ambient temperature by compressed air. With a nitrogen stream, the solution was concentrated and enough NaOMe in MeOH (25% w/v) was added to increase the pH to around 9. Irradiation of the solution for another 5 minutes at 45° C. produced 2-(1-adamantyl)-Δ$^1$-dehydro-10β-hydroxy-19-nortestosterone that was isolated after concentrating the solution, adjusting the pH with acetic acid to slightly acidic and treatment with ice-cold water. The crude product was purified by column chromatography on silica gel using hexane:ethyl acetate 3:2 (v/v) eluent. Yield 45%. APCI-MS: (M+H)$^+$m/z 423. Also see Example 11 below.

EXAMPLE 10

Microwave-Assisted Synthesis of p-Quinols by Lead(IV) Acetate Oxidation

One conventional method for the synthesis of steroidal p-quinols uses lead (IV) acetate oxidizing agent and very long (30$^+$ h) reaction time resulting in numerous side-reactions that make the isolation of the desired p-quinol cumbersome and very inefficient (Gold A M, Schwenk E., "Synthesis and reactions of steroidal quinols." J. Am. Chem. Soc., 80:5683 (1958)). In another method, m-chloroperoxybenzoic acid is used for the oxidation with dibenzoil peroxide radical initiation upon light irradiation, and 3.5-24 h of reaction time is required to complete the reaction depending on the phenolic compound to be oxidized ((a) Solaja, B. A.; Milic, D. R.; Gasic, M. J. Tetrahed. Lett., 37, 3765 (1996); (b) Milic, D. R.; Gasic, M. J.; Muster, W.; Csanádi, J. J.; Solaja, B. A. Tetrahedron, 53, 14073 (1997)). While certain p-quinols (2a,b; see Table 4 below) were able to be obtained with about 50% yield from estrone (1a; see Table 4 below) and 17β-estradiol (1b; see Table 4 below) within 6 h by using the latter method, A-ring substituted estrogens (e.g., 1c; see Table 4 below), 17β-alkyl ether derivatives of 1b (e.g., 1d; see Table 4 below) or simple p-alkylphenols such as 5a,b (see Table 4 below) did not convert to the corresponding p-quinols with appreciable yields, neither by radical-initiated oxidation with m-chloroperoxybenzoic acid nor with the conventional Pb(OAc)$_4$ oxidation, even after prolonged reaction times (>24 h).

Microwave-assisted organic synthesis (MAOS) has received considerable attention in recent years because of the rapid synthesis of a variety of organic compounds (Kappe, C. O., Angew. Chem. Int. Eng. Ed., 43, 6250 (2005)). MAOS was used for the preparation of p-quinols of the invention. It was reasoned that by significantly shortening the reaction time upon microwave irradiation when Pb(OAc)$_4$ is used for the oxidation, the extent of side-reactions would be reduced and, thus, increase the yield and simplify the isolation process. Further, amount of lead salt traditionally used [1:3 molar ratio of the starting material and Pb(OAc)$_4$] could be reduced.

Experiments were carried out in CEM (Matthews, N.C.) Discover monomode microwave apparatus, operating at a frequency of 2.45 GHz with continuous irradiation power of 0 to 300 W, was used. The temperature (measured by infrared detection) was maintained at 40° C. by continuous feedback control and power modulation. The closed-vessel reaction under controlled pressure was performed in a glass vessel (capacity 10 mL) sealed with a septum. After irradiation, the reaction vessel was cooled rapidly to ambient temperature by compressed air cooling; the phenolic compounds (1 eq) were dissolved in glacial acetic acid, and Pb(OAc)$_4$ (1.5 eq) was added. After 15-20 minutes of irradiation, the reactions were complete (monitored by TLC). With a nitrogen stream, the solution was concentrated and NaOMe in MeOH (25%, w/v) was added to increase the pH to approximately 9. Irradiation of the solution for another 5 min produced the target p-quinols that were isolated after treatment with ice-cold water. The crude products were obtained (in contrast with black oils yielded by the conventional method; Gold A M, Schwenk E., *J. Am. Chem. Soc.,* 80:5683 (1958)) as pale-yellow solids that were purified by flash column chromatography on silica gel.

Indeed, as illustrated in Scheme VI below, the p-quinol formation was complete within 15-20 min (monitored by TLC) when microwave irradiation was applied for the oxidation of all of the phenolic compounds of interest (1a-d, 4, and 5a,b; see Table 4 below) using only 1.5 eq of Pb(OAc)$_4$ in glacial acetic acid. The intermediate p-quinol acetates were not isolated, but hydrolyzed after removal of the solvent and by subsequent addition of NaOMe in MeOH to the target p-quinols under microwave irradiation within 5 min, while the original procedure (Gold A M, Schwenk E., *J. Am. Chem. Soc.,* 80:5683 (1958)) called for approximately 12 h of reaction time to hydrolyze the intermediates. Moreover, microwave-assisted synthesis was suitable for the rapid oxidation of A-ring substituted estrogens (e.g.; 1c), while conventional methods were not applicable and/or efficient for these type of compounds. After flash chromatographic purification, 2a-d, 4, and 6a,b were obtained with consistent 40-50% yields (Table 4 below).

Taken together, the MAOS approach presented here significantly reduced the reaction time and the amount of Pb(OAc)$_4$ used for the oxidation of p-alkyl phenols. The procedure provided, therefore, an increased throughput and more ecofriendly route to obtain p-quinols of the invention. This method also provides a convenient, fast, reliable and universally applicable route for the synthesis of the subject quinol compounds, and is useful for obtaining valuable intermediates that allow for the synthesis of many complex organic molecules.

TABLE 4

Comparison of yields and reaction times between conventional methods and the microwave-assisted procedure for the synthesis of p-quinols using Pb(OAc)$_4$ [scale: 2 mmol, equiv. ratio of starting material/Pb(OAc)$_4$ = 1:1.5].

| Target Compound | Conventional Methods | | Microwave-Assisted Synthesis | |
|---|---|---|---|---|
| | Yield (%)[a] | Time (h) | Yield (%)[a] | Time (min)[b] |
| 2a | 20[b]/54[c] | 36[d]/4[c] | 50 | 30 |
| 2b | 10[b]/45[c] | 36[d]/6[c] | 45 | 30 |
| 2c | <5[b,c] | 24[c,d] | 40 | 30 |
| 2d | <5[b,c] | 24[c,d] | 50 | 25 |
| 4 | <10[b,c] | 5[d] | 47 | 25 |
| 6a | <10[c] | 24[c] | 40 | 25 |
| 6b | <5[b,c] | 24[c,d] | 45 | 30 |

[a]Yield after purification by flash chromatography;
[b]By radical-initiated oxidation with m-chloroperoxybenzoic acid, according to Gold A M, Schwenk E., J. Am. Chem. Soc., 80: 5683 (1958);
[c]By Pb(OAc)$_4$ oxidation, according to reference 7 Solaja, B. A.; Milic, D. R.; Gasic, M. J. Tetrahed. Lett., 37, 3765 (1996); and Milic, D. R.; Gasic, M. J.; Muster, W.; Csanádi, J. J.; Solaja, B. A. Tetrahedron, 53, 14073 (1997);
[d]Combined reaction time (oxidation and hydrolysis).

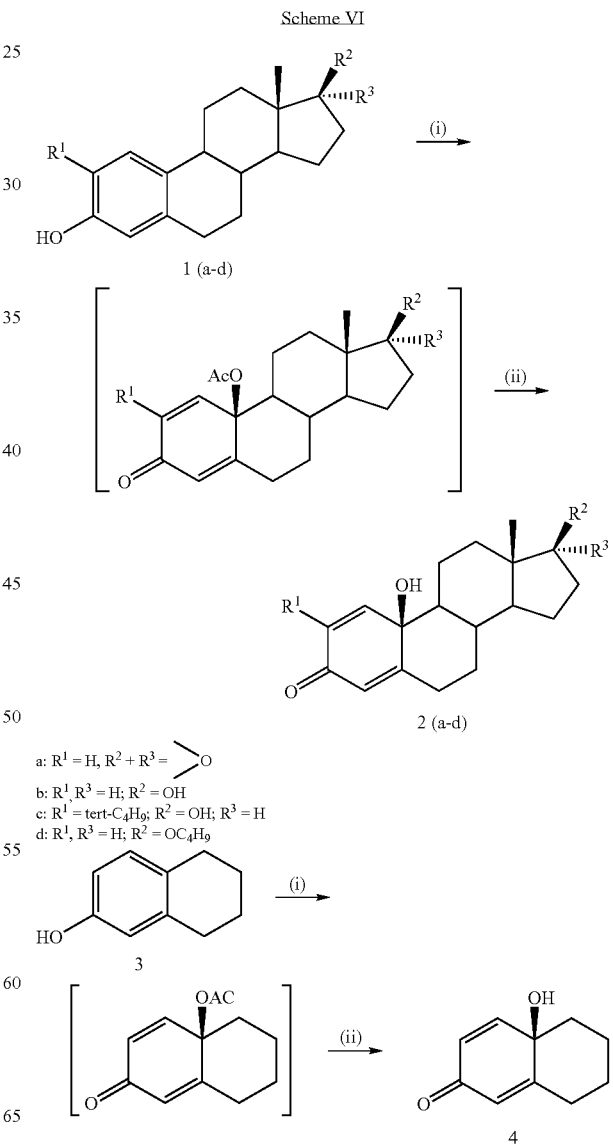

Scheme VI

-continued

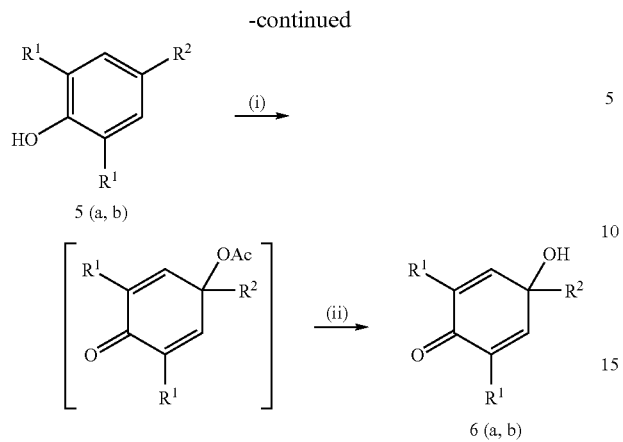

a: R¹ = tert-C₄H₉, R² = CH₃
b: R¹ = H, R² = C₈H₁₇

(i) Pb(OAc)₄, AcOH; (ii) NaOMe, MeOH

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A quinol that is converted to a biologically active 2-(1-adamantyl)-estra-1,3,5(10)-triene-3,17β-diol and which has the structure:

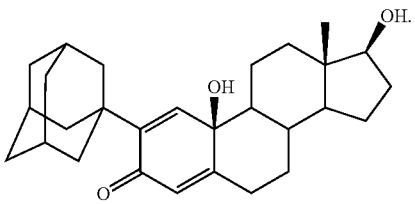

2. A pharmaceutical composition comprising a quinol that is converted to a biologically active estrogen compound via enzyme catalyzed reduction, wherein said composition further comprises a pharmaceutical acceptable carrier, wherein the quinol has the structure:

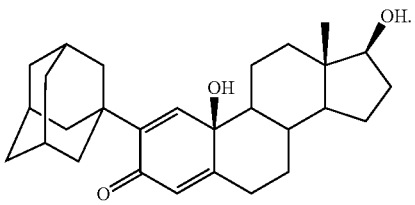

* * * * *

UNITED STATES PATENT AND TRADEMARK OFFICE
CERTIFICATE OF CORRECTION

PATENT NO. : 7,534,779 B2  Page 1 of 1
APPLICATION NO. : 11/838676
DATED : May 19, 2009
INVENTOR(S) : Laszlo Prokai and Katalin Prokai It is certified that error appears in the above-identified patent and that said Letters Patent is hereby corrected as shown below:

Column 18, Line 63

" 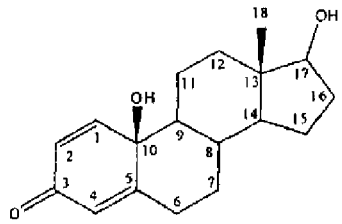 " should read 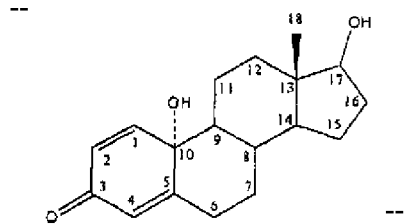 --

Column 19, Line 23

" 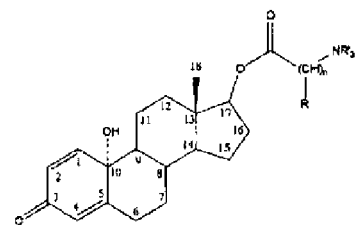 " should read 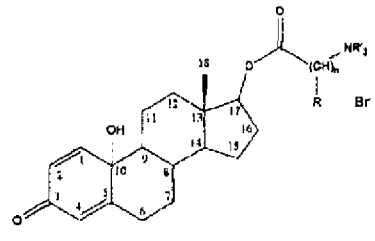 --

Signed and Sealed this

Eleventh Day of August, 2009

David J. Kappos
*Director of the United States Patent and Trademark Office*